(12) United States Patent
Stewart

(10) Patent No.: US 9,557,106 B2
(45) Date of Patent: *Jan. 31, 2017

(54) HELMET DRYER

(71) Applicant: Michael Stewart, Detroit, MI (US)

(72) Inventor: Michael Stewart, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/558,510

(22) Filed: Dec. 2, 2014

(65) Prior Publication Data

US 2015/0184934 A1 Jul. 2, 2015

Related U.S. Application Data

(63) Continuation of application No. 13/591,537, filed on Aug. 22, 2012, now Pat. No. 8,898,929.

(60) Provisional application No. 61/526,843, filed on Aug. 24, 2011.

(51) Int. Cl.
| | |
|---|---|
| *F26B 23/00* | (2006.01) |
| *F26B 3/28* | (2006.01) |
| *D06F 59/04* | (2006.01) |
| *F26B 9/00* | (2006.01) |
| *F26B 21/06* | (2006.01) |

(52) U.S. Cl.
CPC ............... *F26B 3/28* (2013.01); *D06F 59/04* (2013.01); *F26B 3/283* (2013.01); *F26B 9/003* (2013.01); *F26B 21/06* (2013.01); *F26B 23/00* (2013.01)

(58) Field of Classification Search
CPC ............... F26B 3/00; F26B 3/283; F26B 9/00; F26B 9/003; F26B 23/00; D06F 58/00; D06F 58/20; D06F 58/23; D06F 59/00; D06F 59/04

USPC ... 34/90, 104, 105, 381, 413; 223/85; 422/4, 422/24; 454/370; 134/103.2
See application file for complete search history.

(56) References Cited

U.S. PATENT DOCUMENTS

| | | | | |
|---|---|---|---|---|
| 3,507,552 | A | * | 4/1970 | Scott ................... A61F 9/023 351/159.29 |
| 5,049,139 | A | | 9/1991 | Gilchrist |
| 5,555,640 | A | * | 9/1996 | Ou ...................... A47L 19/00 211/133.6 |

(Continued)

FOREIGN PATENT DOCUMENTS

| | | | | | |
|---|---|---|---|---|---|
| AT | DE 102010013183 | A1 | * | 9/2011 | ............ A42B 3/006 |
| CA | EP 2476797 | A1 | * | 7/2012 | ............ D06F 59/02 |

(Continued)

OTHER PUBLICATIONS

Cozy Winters: INNOVA—15 Pair Boot Dryer, Feb. 23, 2005, 1 pg. http://cozywinters.com/shopping/merchant.mv?Screen=PROD&Store_Code=cw&Product . . . .

(Continued)

*Primary Examiner* — Stephen M Gravini
(74) *Attorney, Agent, or Firm* — Harness, Dickey & Pierce, P.L.C.

(57) ABSTRACT

An apparatus for drying headwear is provided, including a main member, at least one light source, and at least one air source. The main member includes an outer surface configured for receiving a glove, and a plurality of apertures disposed along the outer surface. The light source emits a UV-C light, and the air source blows air. The UV-C light from the light source and air from the air source can at least partially pass through the outer surface. The apertures are in communication with at least the air source.

7 Claims, 29 Drawing Sheets

(56) References Cited

U.S. PATENT DOCUMENTS

| | | | |
|---|---|---|---|
| 5,829,157 A * | 11/1998 | Gittens | A45D 20/20 34/99 |
| 6,085,436 A | 7/2000 | Peet | |
| 6,267,782 B1 | 7/2001 | Ogle et al. | |
| 6,553,687 B1 * | 4/2003 | Leamon, Jr. | F26B 9/003 34/103 |
| 6,796,053 B2 | 9/2004 | Lurie | |
| 7,328,708 B2 | 2/2008 | Malak | |
| 8,621,762 B2 * | 1/2014 | Beckett | D06F 59/02 134/13 |
| 8,898,929 B2 * | 12/2014 | Stewart | D06F 59/04 134/103.2 |
| 8,966,781 B1 * | 3/2015 | McKernan | A61L 2/07 211/189 |
| 9,015,955 B2 * | 4/2015 | Vezina | D06F 58/14 211/182 |
| 2007/0086914 A1 | 4/2007 | Antinozzi | |
| 2008/0118411 A1 | 5/2008 | D'Arinzo | |
| 2008/0199354 A1 | 8/2008 | Gordon | |
| 2009/0004047 A1 | 1/2009 | Hunter et al. | |
| 2010/0229281 A1 | 9/2010 | Neuser et al. | |
| 2011/0197464 A1 | 8/2011 | Chappell et al. | |
| 2012/0102620 A1 | 5/2012 | Neuser et al. | |
| 2012/0156094 A1 | 6/2012 | Gordon | |
| 2013/0180124 A1 * | 7/2013 | Durham | A47L 23/205 34/237 |
| 2013/0212900 A1 | 8/2013 | Stewart | |
| 2015/0184934 A1 * | 7/2015 | Stewart | D06F 59/04 34/275 |

FOREIGN PATENT DOCUMENTS

| | | | |
|---|---|---|---|
| KR | 101172513 B1 * | 8/2012 | |
| WO | WO 2007012130 A1 | 2/2007 | |

OTHER PUBLICATIONS

Germicidal ultraviolet UVF-C lamp spectrum chart—All germicidal lamps are not created equal, Apr. 22, 2006, 5 pgs, http://www.negativeiongenerators.com/UV-C spectrum.html.

* cited by examiner

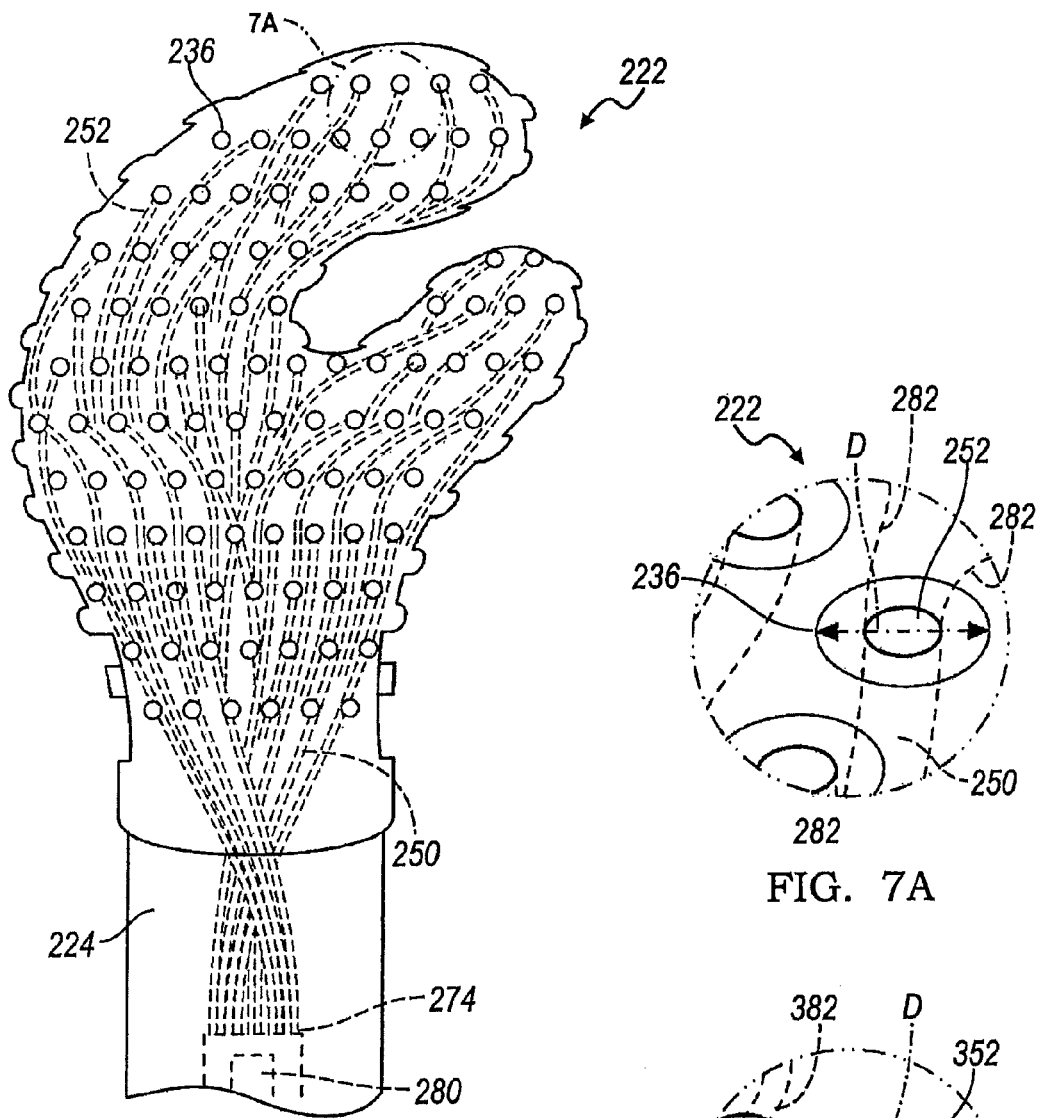
FIG. 7
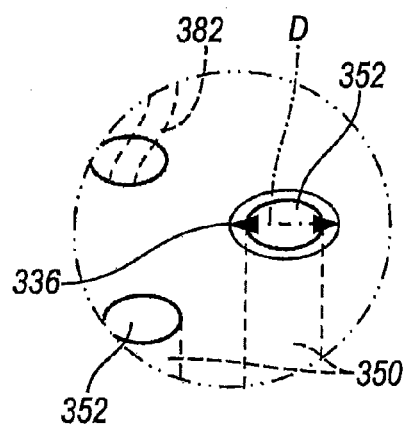
FIG. 7A
FIG. 7B

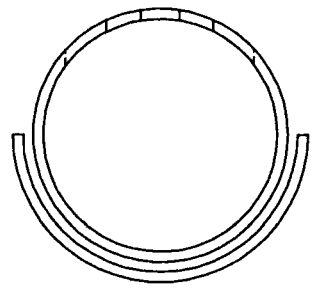
FIG 21E
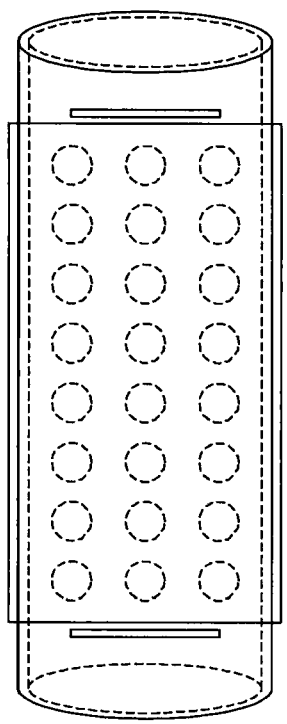 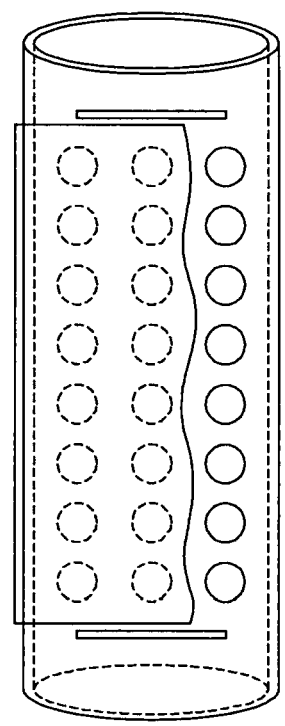
FIG 21C                    FIG 21D

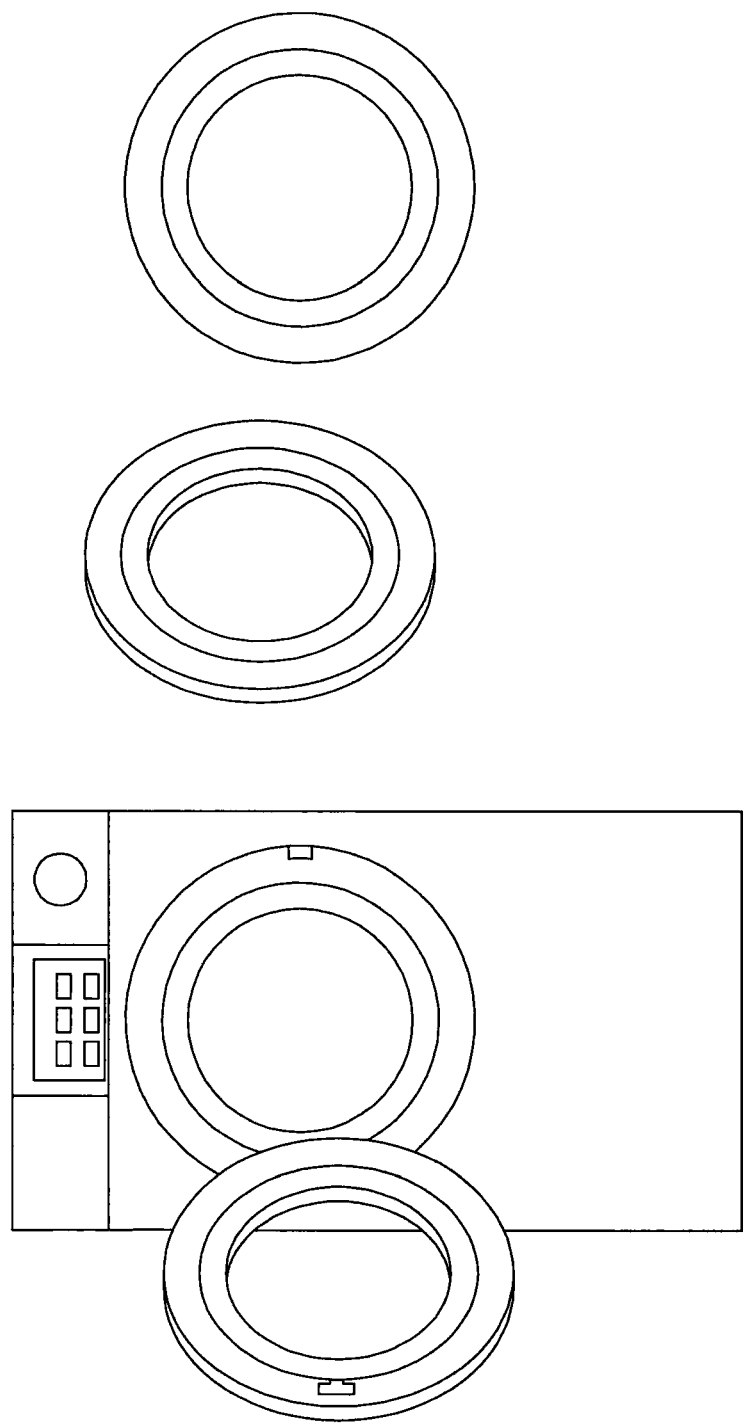

HELMET DRYER

CROSS-REFERENCE TO RELATED APPLICATIONS

This application is a continuation-in-part of U.S. patent application Ser. No. 13/591,537 filed on Aug. 22, 2012, which claims the benefit of U.S. Provisional Application No. 61/526,843, filed on Aug. 24, 2011. The entire disclosure of the above application is incorporated herein by reference.

FIELD

The present disclosure relates generally to a glove dryer and, more particularly, to a glove dryer including a main member configured for receiving a glove, where the main member includes an outer surface that allows ultraviolet (UV-C) light and air to at least partially pass through.

BACKGROUND

This section provides background information related to the present disclosure which is not necessarily prior art.

Glove dryers are frequently used to dry moisture that is trapped inside of a glove. This moisture is generated primarily from the palm and fingers of a user's hand. Repeatedly soaking a leather glove with moisture will cause the leather to become stiff and brittle over time, and ultimately the leather with tear. Moisture that is trapped inside of the glove also encourages growth of bacteria and microorganisms. The bacteria and microorganisms that are trapped inside of the glove create an unpleasant odor.

Moreover, moisture that is generated from the user's hand also contains salt. Salt is especially harmful to leather gloves because salt also hardens the leather. Traditional grove dryers only evaporate moisture that is trapped inside the glove. These dryers cannot reduce the salt or disinfect the glove to reduce the bacteria and microorganisms that collect inside of the glove.

Gloves that are used in the Japanese sport of kendo (sometimes called kote), include a distinctive design where the kendo glove is shaped in a hooked configuration, similar to a boxing glove. These gloves generally are padded with hair, such as deer hair that is biodegradable. Kendo gloves usually include palm portions that are constructed from leather. The palms of kendo gloves are leather because this material is flexible, thereby allowing the user to grasp a sword easily. However, moisture and salt from the user's palm over time causes the leather portion to become stiff and brittle, and eventually the leather will tear. This tearing is especially problematic for the user because some kendo gloves are extremely expensive (at least several hundred dollars) and can be costly to replace.

Thus, there exists a need for a glove dryer that will reduce moisture and contaminants that are trapped inside of a glove when compared to the current glove dryers that are available today.

SUMMARY

This section provides a general summary of the disclosure, and is not a comprehensive disclosure of its full scope or all of its features.

According to the present teachings, an apparatus for drying gloves is presented. The application has a main member having an outer surface configured to be positioned within a glove. The main member defines a plurality of apertures fluidly coupled to an air pressure or vacuum source. A UV-C light is coupled to the exterior surface of the member to apply UV-C radiation to the inside of the garment.

Further, according to the present teachings, an apparatus for drying a garment is provided. The apparatus has a main member having an outer surface. The outer surface defines a plurality of apertures fluidly coupled to a vacuum or an air pressure source. The outer surface further defines a plurality of grooves or channels. A UV-C light source is provided to provide UV-C radiation to an interior surface of the garment.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 is a partially cross-sectional view of another alternative exemplary illustration of the main member;

FIG. 7A is an enlarged view of Region A in FIG. 7;

FIG. 7B is an alternative illustration of FIG. 7A;

FIGS. 25a-25e and 26 represent a cloths drier according to the present teachings.

Corresponding reference numerals indicate corresponding parts throughout the several views of the drawings.

DETAILED DESCRIPTION

Figure 1:
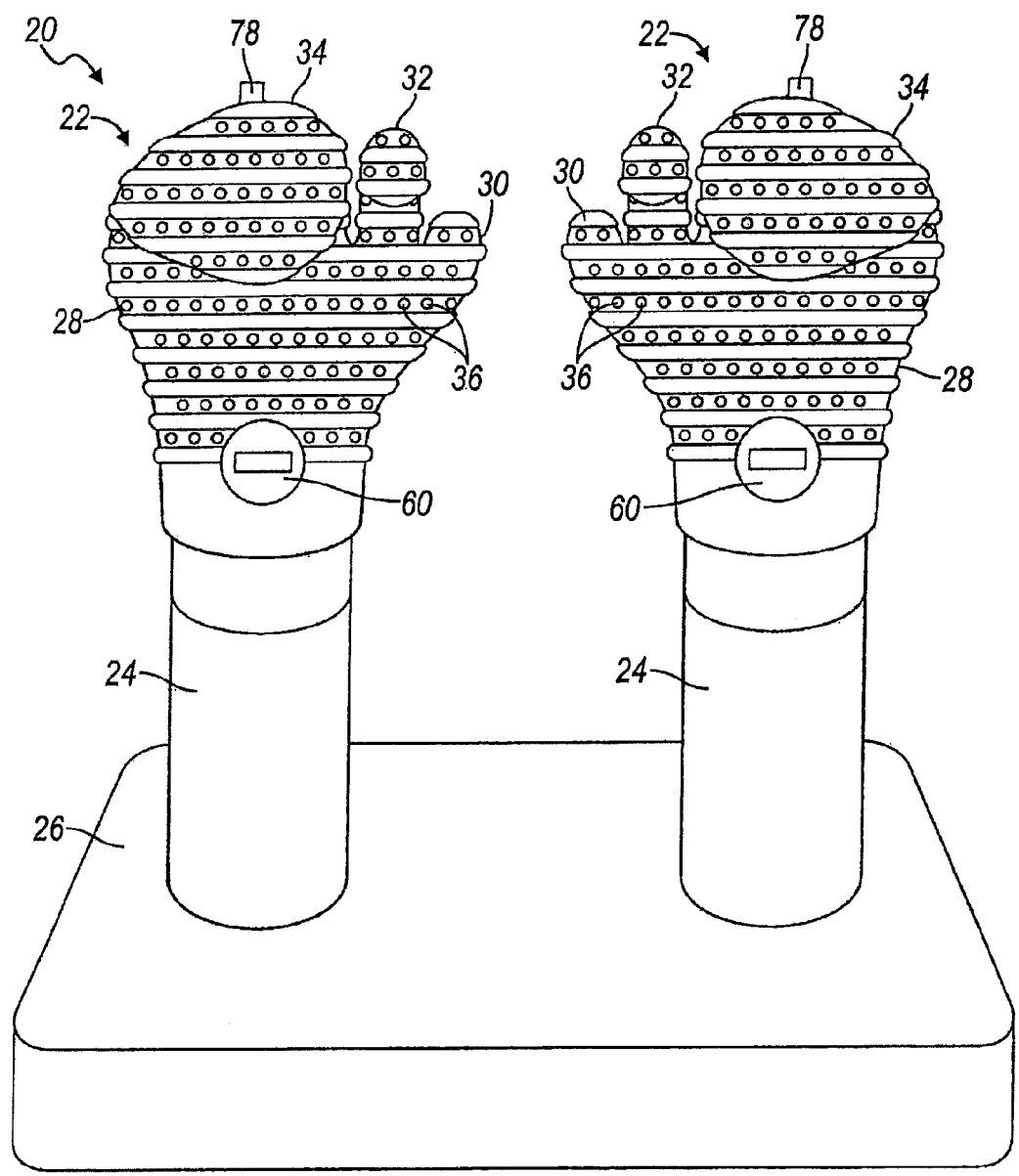
FIG. 1 is an elevational perspective view of the glove dryer with a base, two conduits and two main members that are configured for receiving a glove.

Example embodiments will now be described more fully with reference to the accompanying drawings.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

According to various exemplary illustrations described herein, a main member is provided and includes an outer surface configured for receiving a glove. The main member includes a plurality of apertures disposed along the outer surface. At least one light source for emitting a UV and preferably UV-C light, and at least one air source for blowing air are also provided. The apertures located along the outer surface of the main member are in communication with at least the air source. UV-C light from the light source (such as a OLED, SLD) and air from the air source can at least partially pass though the outer surface. The main member is constructed from a material with a transparency that allows for UV-C light from the air source to at least partially pass through. Alternatively, the light source is at least one optical fiber, wherein at least one aperture of the main member receives an end of the optical fiber, where the end emits the UV-C light. Finally, the glove dryer may also include a spray source for spraying a solution, where the spray source is in communication with the apertures of the main member.

Turning now to the drawings and in particular to FIG. 1, a glove dryer 20 is illustrated in FIG. 1 having at least one main member 22, at least one conduit 24, and a base 26. Each of the main members 22 are in communication with one of the conduits 24. The conduit portion 24 may additionally be perforated to allow air flow into the wrist portion of the glove. Optionally, these perforations may be baffled to regulate air flow. In the illustration as shown, the main members 22 each include an outer surface 28 that is configured for receiving a left glove and a right glove respectively. It should be noted that while FIG. 1 illustrates the main members 22 configured for receiving gloves, the main members 22 may also be configured to receive other articles such as, but not limited to, boots. Moreover, although FIG. 1 illustrates the glove dryer 20 including two main members 22, any number of main members 22 may be included.

The main members 22 each include at least a first member 30 for receiving a thumb of a glove, a second member 32 for receiving an index finger of a glove, and a third member 34 for receiving the remaining fingers of a glove. As discussed in greater detail below, the main member 22 may also include a fourth member and a fifth member as well, for receiving the ring finger and the little finger of a traditional five-finger glove. The main members 22 also include a plurality of apertures 36 that are disposed along the outer surface 28. The main members 22 also include an adjustable baffle 60. As discussed in greater detail below, the baffle 60 is to increase or decrease air flow inside of the main member 22.

Figure 2:
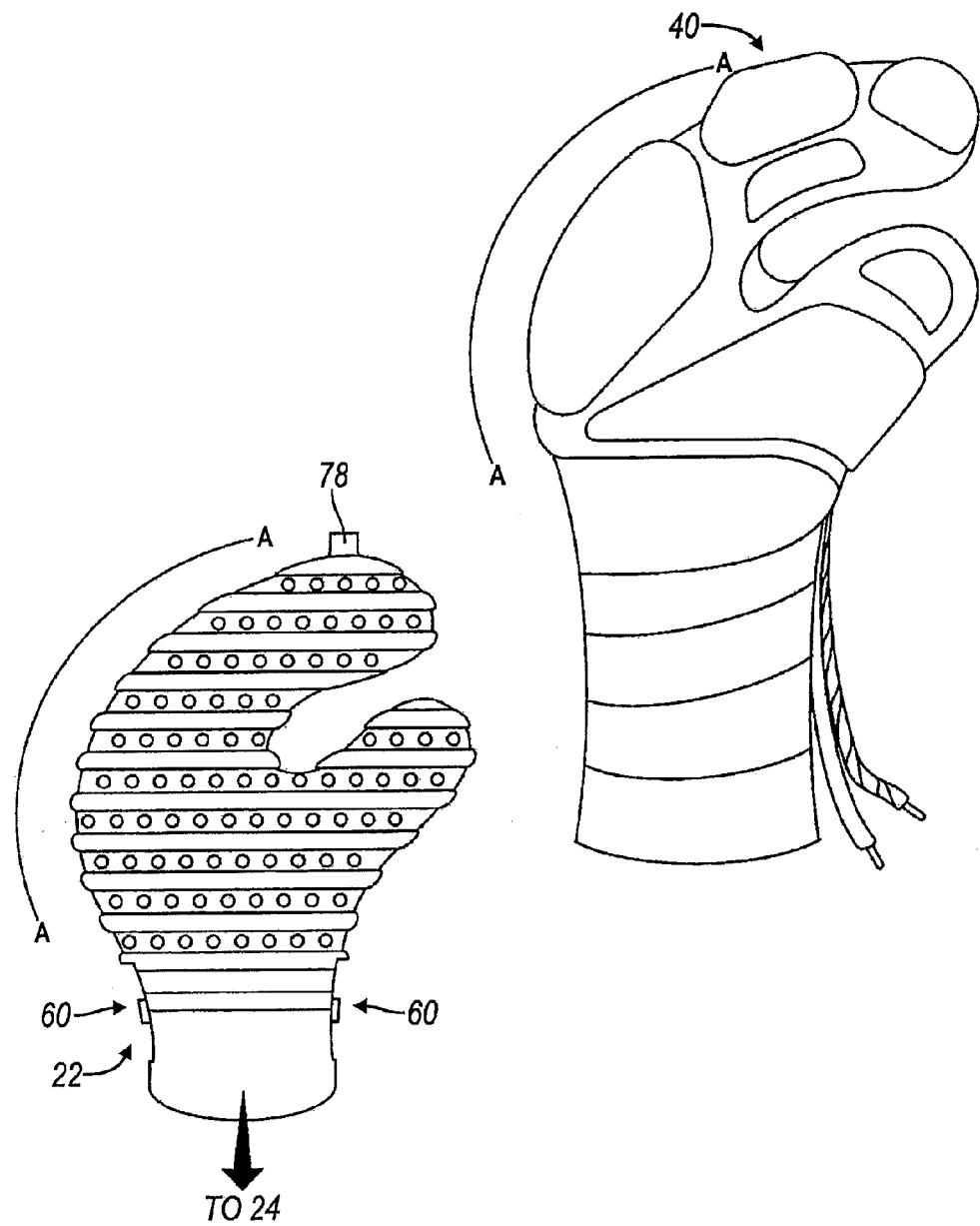
FIG. 2 is an elevational perspective view of one of the main members in FIG. 1 and a glove.

FIG. 1 illustrates the main members 22 configured to receive a glove and, more specifically, the outer surface 28 is configured to receive a glove that is used in the Japanese sport of kendo. As best seen in FIG. 2, the main member 22 is contoured along a curved axis A-A. The curved axis A-A is contoured to match the hooked configuration of a kendo glove 40. That is, the main members 22 are in a hooked configuration, and adapted to fit under the glove 40. Having the main members 22 contoured along the curved axis A-A is advantageous, because when the glove 40 is placed on one of the main members 22, the glove 40 is dried and disinfected while in the hooked configuration, as discussed in greater detail below. That is, the main member 22 is configured such that the glove 40 can be dried in the natural shape.

Figure 3:
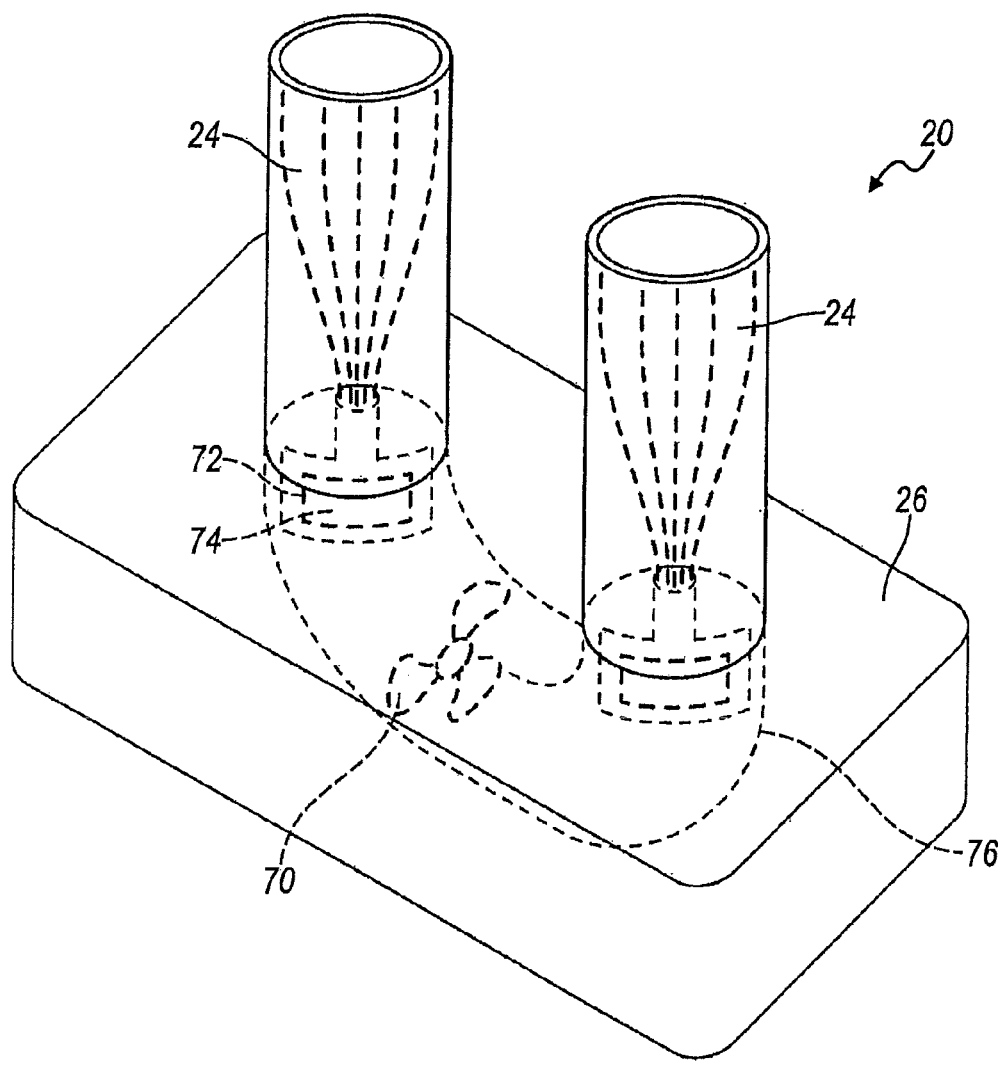
FIG. 3 is a partially cross-sectional view of the base and the conduits.

FIG. 3 is a partially sectional view of the conduits 24 and the base 26. The main members 22 may be removable from the conduits 24. For example, in some cases it may be easier to clean the main member 22 by removing the main members 22 from the conduits 24 first. A passageway 76 is located inside of the base 26 and connects one of the conduits 24 to the other conduit 24. An air source, such as a fan 70, is used to generate airflow to both the conduits 24 which, in turn, are in communication with the main members 22. Although FIG. 3 illustrates the fan 70 as an air source, it should be noted that any device capable of producing airflow may be used. The baffle 60, as seen in FIGS. 1-2, is used to regulate the amount of airflow to the inside surface 84 of the glove 40 and, therefore, the amount of air from the fan 70 can be increased or decreased, depending on what the user desires.

In one illustration, each of the conduits 24 also include a heat source to warm the air from the fan 70. FIG. 3 illustrates a heater core 72 located inside the passageway 76. Including a heat source such as the heater core 72 is advantageous, because heated air will accelerate drying of the gloves 40.

An ultraviolet light source 74 is included in the glove dryer 20 as well. The ultraviolet light source 74 emits UV-C light (also known as germicidal UV light). UV-C is ultraviolet light in the C bandwidth of the ultraviolet light spectrum. Ultraviolet irradiation in the C bandwidth (UV-C) is used for disinfection purposes because the UV-C light kills microorganisms, mold and bacteria that are trapped inside of the glove 40. In one example, the ultraviolet light source 74 is a mercury-vapor lamp that emits UV-C light; however, it should be noted that any light source that emits UV-C rays may be used as well. In one illustration, the ultraviolet light source 74 also produces ozone ($O_3$); however, an ultraviolet light source 74 that does not produce ozone may be used as well. Ozone and UV-C light are combined with moisture that is trapped inside the glove 40 to remove odors. More specifically, the combination of ozone and UV-C light with moisture produces chemicals, such as hydroxyl radicals (—OH), which are purifying agents that neutralize unpleasant odors that are trapped inside of the glove 40.

It should be noted that prolonged exposure to UV-C light that is emitted from the ultraviolet light source 74 may be harmful to humans. As a result, as seen in FIGS. 1-2, a safety device 78 is included along the outer surface 28 of the main members 22. The safety device 78 detects if the glove 40 is installed on the main member 22. The ultraviolet light source 74 is unable to emit UV-C light unless the glove 40 is secured to the main member 22. In the illustration as shown in both of FIGS. 1-2, the safety device 78 is located on the third member 34. However, it should be noted that the safety device 78 may be located anywhere along the main member 22. In one illustration, the safety device 78 is a sensor that detects the presence of the glove 40 along the outer surface 28. However, the safety device 78 can be any device that is able to detect whether the glove 40 is installed along the outer surface 28 of the main member 22. More than one safety sensor 78 can also be applied along the outer surface 28 of each of the main members 22 as well. In another example, the safety device 78 can be a shield or a hood that protects against UV-C light that is well-known in the art, and covers the main members 22 when in use.

Because the glove 40 may contain salt that is emitted from a user's hand, the glove dryer 20 may also include a spray source 80. The spray source 80 is filled with a solution 82 that breaks down salt that collects inside of the glove 40. The solution 82 may also include ingredients that are used to deodorize the inside of the glove 40 such as, but not limited to, cyclodextrin. Additionally, the solution 82 may also include an ingredient to the inside of the glove 40 such as, but not limited to, isopropyl alcohol or chloroxylenol. In one illustration, the solution 82 may include each of the ingredients that breakdown salt, deodorize the inside of the glove 40, and also disinfect the inside of the glove 40. Alternatively, the solution 82 may only include one of the ingredients that break down salt, disinfect, and deodorize. The solution 82 is applied to the inside of the glove 40 after UV-C light from the ultraviolet light source 74 reduces microorganisms, mold, and bacteria that are trapped inside of the glove 40, as discussed in greater detail below.

Figures 4, 4A:
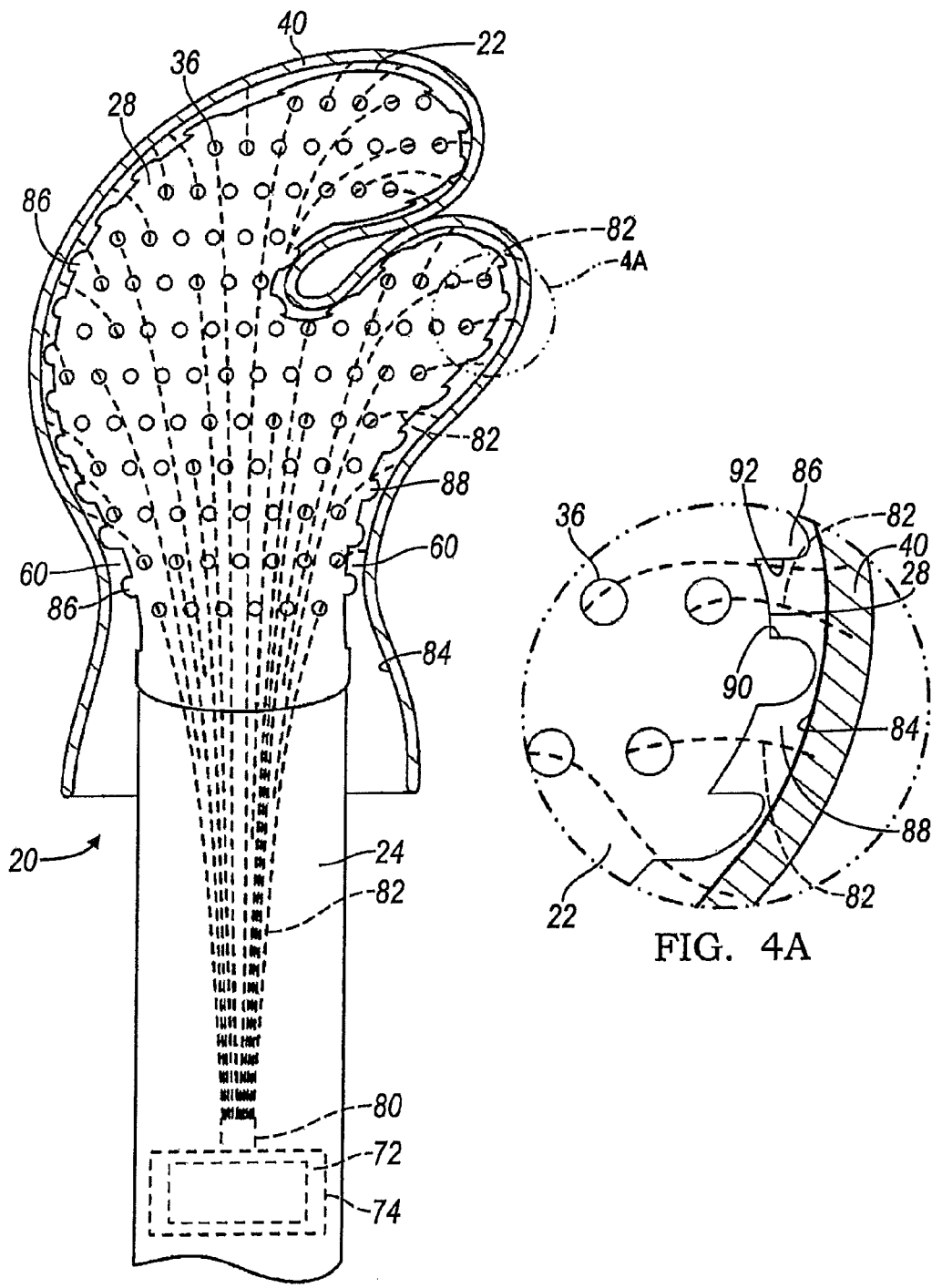
FIG. 4 is a partially cross-sectional view of one of the main members receiving the glove and the conduit.
FIG. 4A is an enlarged view of Region 4A in FIG. 4.

FIG. 4 is a partially cross-sectional view of the conduit 24, one of the main members 22, and the glove 40. The apertures 36 of the main member 22 are in communication with air from the fan 70 (not shown in FIG. 4), ozone generated from the ultraviolet light source 74, and the solution 82 from the spray source 80. Therefore, air from the fan 70, ozone from the ultraviolet light source 74, and the solution 82 can at least partially pass through the outer surface 28 by way of the apertures 36.

In the illustration as shown, the main member 22 is constructed from a material such as, but not limited to, a polymer that includes a transparency that allows for UV-C light from the ultraviolet light source 74 to at least partially pass through the outer surface 28. A UV stabilizer may be added to the material because some types of polymers include a bond structure that is degraded by UV light. In another alternative illustration as discussed below, the ultraviolet light source 74 may be in direct communication with the apertures 36. Therefore, as seen in FIG. 4, the apertures 36 allow for air, ozone, and the solution 82 to pass from the glove dryer 20 to an inner surface 84 of the glove 40. Because the main member 22 is constructed from a material that will at least partially allow for UV-C light to pass though the outer surface 28, UV-C light will also contact the inner surface 84 of the glove 40.

The outer surface 28 also includes a series of horizontally oriented raised portions 86 for creating an airflow space 88 between the main member 22 and the glove 40. The apertures 36 are located between the raised portions 86. Indeed, as best seen in FIG. 4A, an upper surface 90 of one of the raised portions 86, a lower surface 92 of one of the raised portions 86, and the outer surface 28 of the main member cooperate with the inner surface 84 of the glove 40 to form the airflow space 88. The airflow space 88 is advantageous because the airflow space 88 creates a volume of space that permits for the flow of air, ozone, and the solution 82 between the main member 22 and the inside surface 84 of the glove 40. Thus, as may be seen, the airflow space 88 allows air, ozone, and the solution 82 from the main member 22 to contact the inside surface 84 of the glove 40.

Further, the outer surface 28 may include an anti-bacterial or anti-microbial treatment, such as a metal ion, as disclosed in U.S. Pat. Nos. 5,049,139 and 6,267,782. An example would be a silver ion impregnated soluble glass coating.

Figure 5:
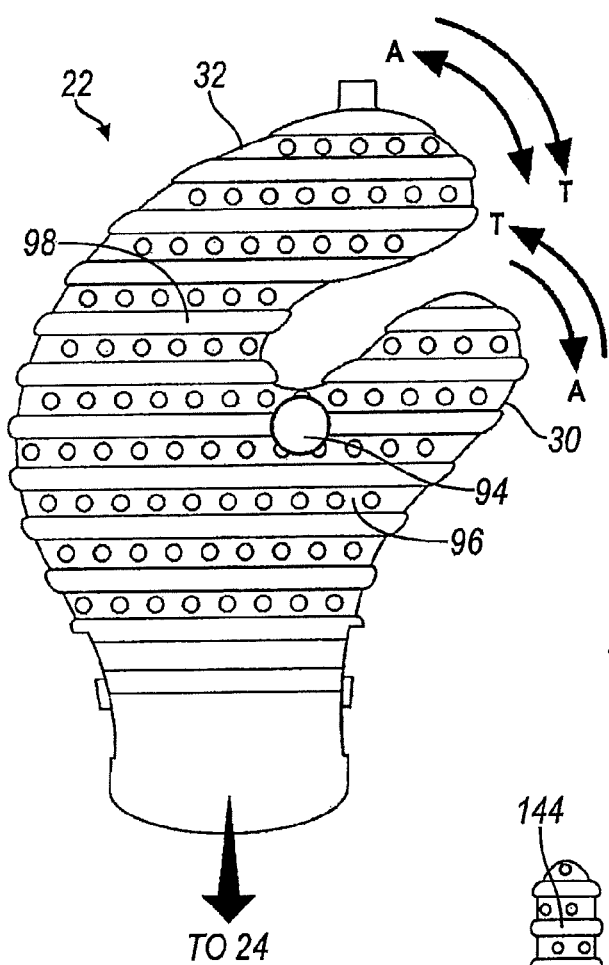
FIG. 5 is an elevational perspective view of one of the main members in FIG. 1 including an articulating point.

FIG. 5 illustrates an articulating point 94 that is located between the first member 30 and the second member 32 of the main member 22. The articulating point 94 is used to move the first member 30 and the second member 32 towards each other in a direction T and away from each other in a direction A. The articulating point 94 is used to adjust the first and second members 30 and 32 to adapt to the shape of the glove 40 in a variety of configurations. More specifically, the articulating point 94 is used to adjust the first and second members 30 and 32 with the corresponding thumb and the index finger of the glove 40. The first member 30 is selectively articulated about a first member base 96 and the second member 32 is selectively articulated about a second member base 98. Thus, the first member 30 and the second member 32 of the main member 22 are selectively adjustable to match the configuration of the glove 40.

Figure 6:
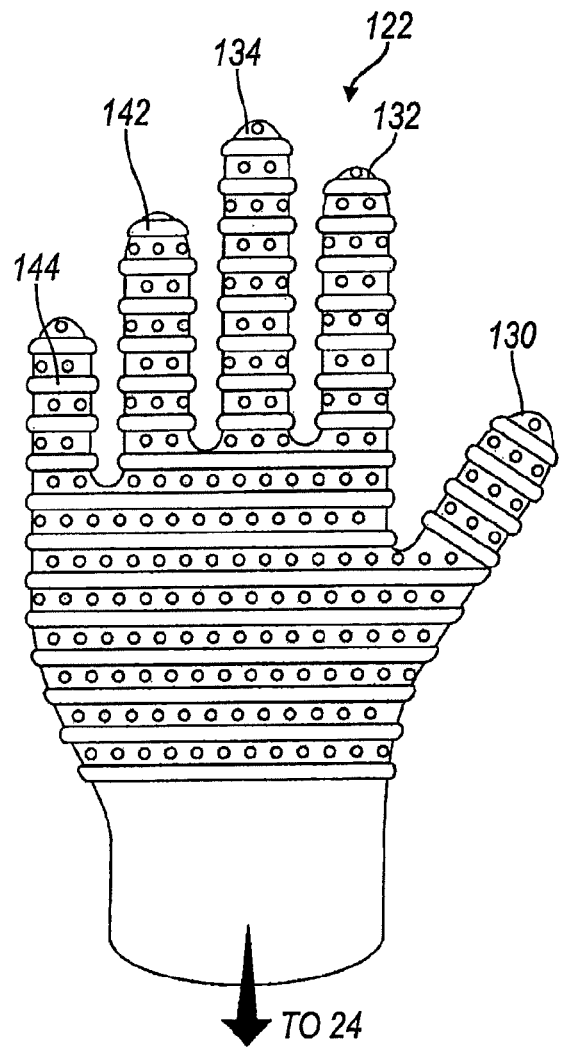
FIG. 6 is an alternative exemplary illustration of the main member.

In one alternative illustration, as best seen in FIG. 6, the main member 122 includes a first member 130, a second member 132, a third member 134 for only receiving the middle finger of a glove, a fourth member 142 for receiving the ring finger of the glove, and a fifth member 144 for receiving the little finger of a glove. The main member 122 may be used to dry a kendo glove, such as glove 40. Alternatively, because the main member 122 includes the fourth member 142 and the fifth member 144, the main member 122 may also be used to dry a traditional five-finger glove as well.

In another alternative illustration, as seen in FIG. 7, the ultraviolet light source 274 is at least one optical fiber 250. FIG. 7 is a partially sectional view of the main member 222 and the conduit 224. The main member 222 includes a plurality of optical fibers 250, where each of the optical fibers 250 is in communication with one of the apertures 236 of the main member 222. As seen in FIG. 7, the apertures 236 of the main member 222 receive an end 252 of one of the optical fibers 250, where the end 252 emits UV-C light from the ultraviolet light source 274. It should be noted that only a portion of the apertures 236 receive the end 252 of one of the optical fibers 250, and a portion of the apertures 236 do not receive the end 252 of one of the optical fibers 250. Instead, the apertures 236 that do not receive the end 252 of one of the optical fibers 250 are in communication with the fan 70 (not shown in FIG. 7) as well as the spray source 280.

The end 252 of the optical fiber 250 transmits UV-C light from the light source 274. Thus, as may be seen, the apertures 236 that are in communication with the end 252 of one of the optical fibers 250 transmit light to the inside surface 84 of the glove 40. The apertures 236 that are in communication with the fan 270 and the spray source 280 transmit both air and the solution 282 to the inside surface 84 of the glove 40 (not shown in FIG. 7).

In one approach, as seen in FIG. 7A, the apertures 236 include a diameter D that is large enough to accommodate both of the end 252 of the optical fiber 250 and air, ozone and the solution 82. That is, the apertures 236 have enough space to allow for air from the fan 70, ozone from the light source 274 and the solution 282 to pass through, in addition to accommodating the end 252 of the optical fiber 250.

Alternatively, in another illustration as seen in FIG. 7B, the diameter D' of the apertures 336 may only be large enough to accommodate the end 352 of the optical fiber 350. Because the apertures 336 can only accommodate the end 352 of the optical fiber 350, some of the apertures 336 are not in communication with the optical fibers 350. The apertures 336 that do not include one of the optical fibers 350 are instead used to communicate air, ozone, and solution 382 to the inside surface 82 of the glove 40.

Figure 8:
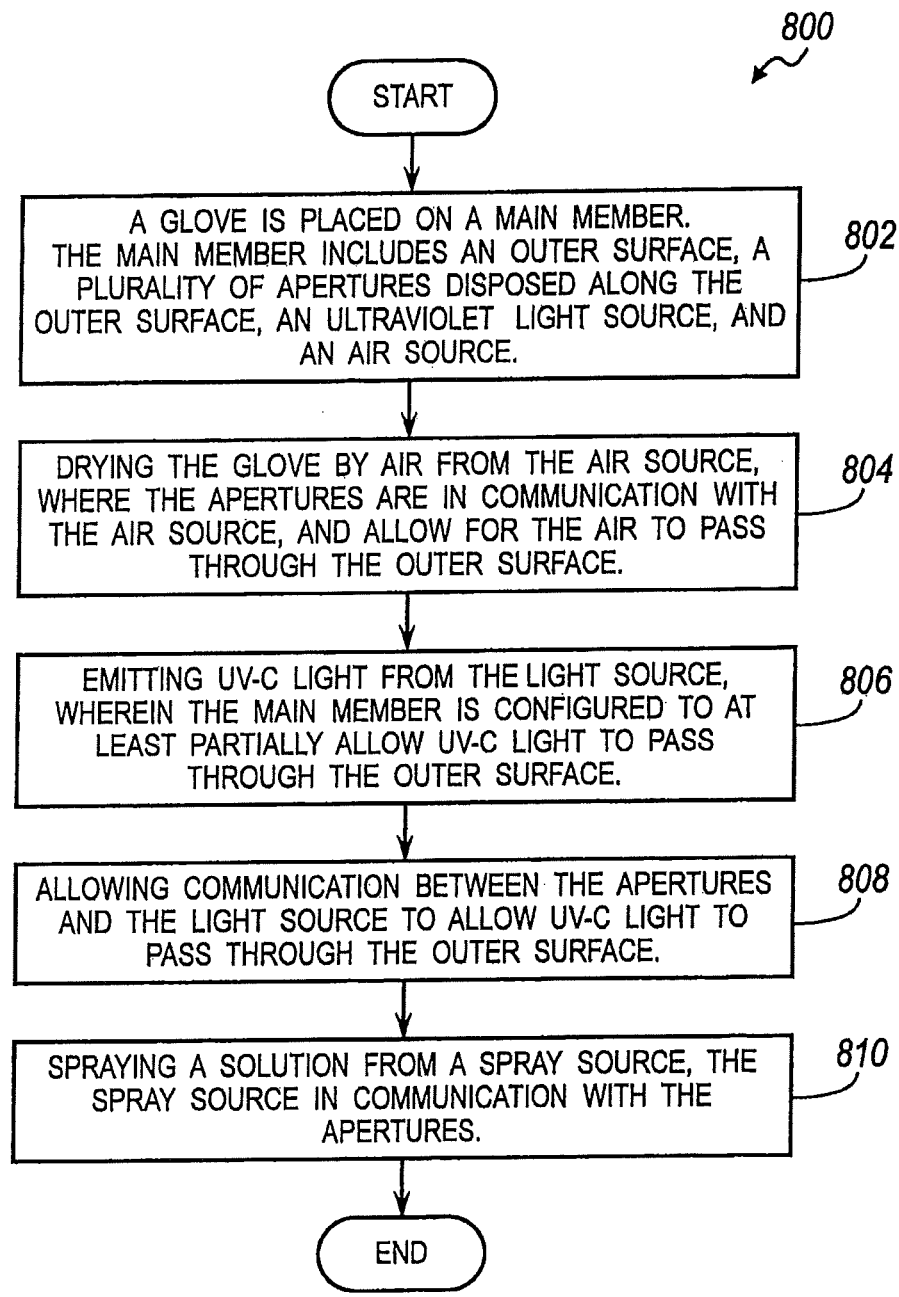
FIG. 8 is a process flow diagram of a method of drying a glove using the glove dryer.

Turning now to FIG. 8, a process 800 for drying a glove using the glove dryer 20 is illustrated. Process 800 may begin at step 802. In step 802, a glove is placed on the main member 22. For example, as discussed above, the main member 22 includes the outer surface 28 that is configured to receive the glove 40. The main member 22 includes a plurality of apertures 36 disposed along the outer surface 28, the ultraviolet light source 74 for emitting ultraviolet light, and the air source, such as the fan 70, for blowing air. Process 800 may then proceed to step 804.

In step 804, the glove is dried by air from the fan 70, or an air source through the apertures 36. For example, as discussed above, the apertures 36 are in communication with the fan 70 and allow for the air from the fan 70 to pass through the outer surface 28. More specifically, the fan 70 generates airflow to both of the conduits 24 that are in communication with the main members 22, and then pass through the apertures 36 located along the outer surface 28. Process 804 may then proceed to step 806.

In step 806, UV-C light is emitted from the ultraviolet light source 74, wherein the main member 22 is configured to at least partially allow UV-C light to pass through the outer surface 28. The main member 22 can be configured in several ways to allow UV-C light to pass through the outer surface 28. For example, as discussed above, the main member 22 is constructed from a material with a transparency that allows for UV-C light from the ultraviolet light source 74 to at least partially pass through the outer surface 28. Alternatively, in another illustration, the ultraviolet light source 274 is at least one optical fiber 250. Process 806 may then proceed to step 808.

In step 808, the apertures 36 are in communication with the ultraviolet light source 274 to allow for UV-C light to pass through the outer surface 28. For example, in one illustration, the main member 222 includes a plurality of optical fibers 250, where each of the optical fibers 250 are in communication with one of the apertures 236 of the main member 222. The apertures 236 of the main member 222 receive the end 252 of one of the optical fibers 250, where the end 252 emits UV-C light from the ultraviolet light source 274. Process 808 may then proceed to step 810.

In step 810, the solution 82 is sprayed from the spray source 80, where the spray source 80 is in communication with apertures 36. For example, as discussed above, the solution 82 may break down salts. The solution 82 may also include ingredients that are used to deodorize the inside of the glove 40. Additionally, the solution 82 may also include an ingredient (such as, for example, anti-bacterial or anti-microbial) to disinfect any remaining bacteria inside of the glove 40 as well. The solution 82 is applied to the inside of the glove 40 after UV-C light from the ultraviolet light source 74 disinfects the microorganisms, mold, and bacterial that are trapped inside of the glove 40. Process 800 may then terminate.

Figure 9:
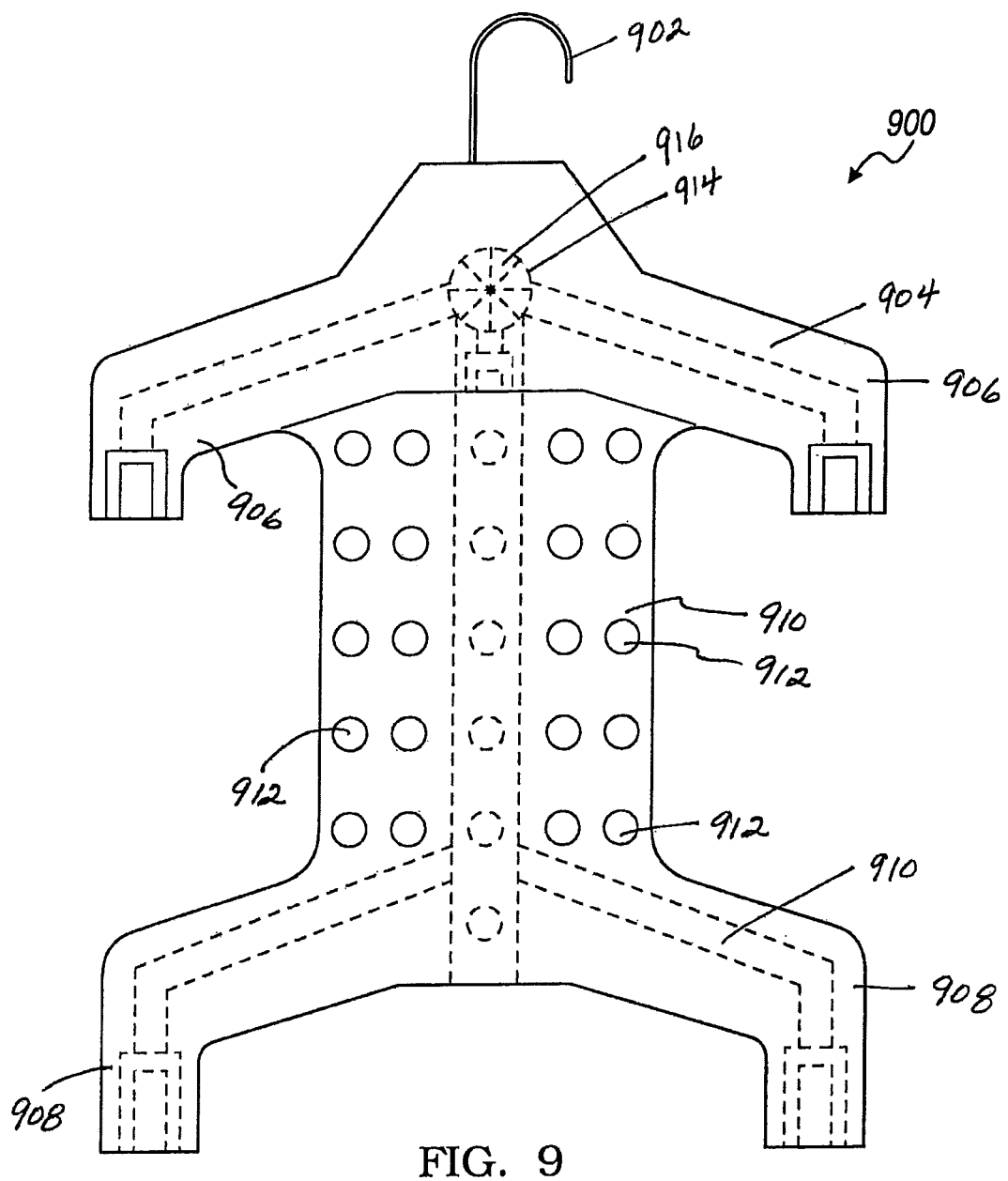
FIGS. 9 and 12 represent alternate dryers according to the present teachings.

FIG. 9 represents an alternate garment dryer 900 according to the present teachings. The garment dryer 900 can have a hook 902 coupled to a body structure 904. The body structure 904 can have a pair of arm members 906 and a pair of leg members 908. The body structure 904 defines an internal chamber 910 fluidly coupled to a plurality of apertures 912 defined within the body structure 904.

Fluidly coupled to the internal chamber 910 is an opening aperture 914 having an associated fan 916 associated therewith. The fan 916 is configured to apply air pressure or a vacuum to the internal chamber 910 and associated apertures 912. It is envisioned the apertures can have a UV-C light and ozone generator source associated therewith as described in any of the embodiments above.

Figure 10:
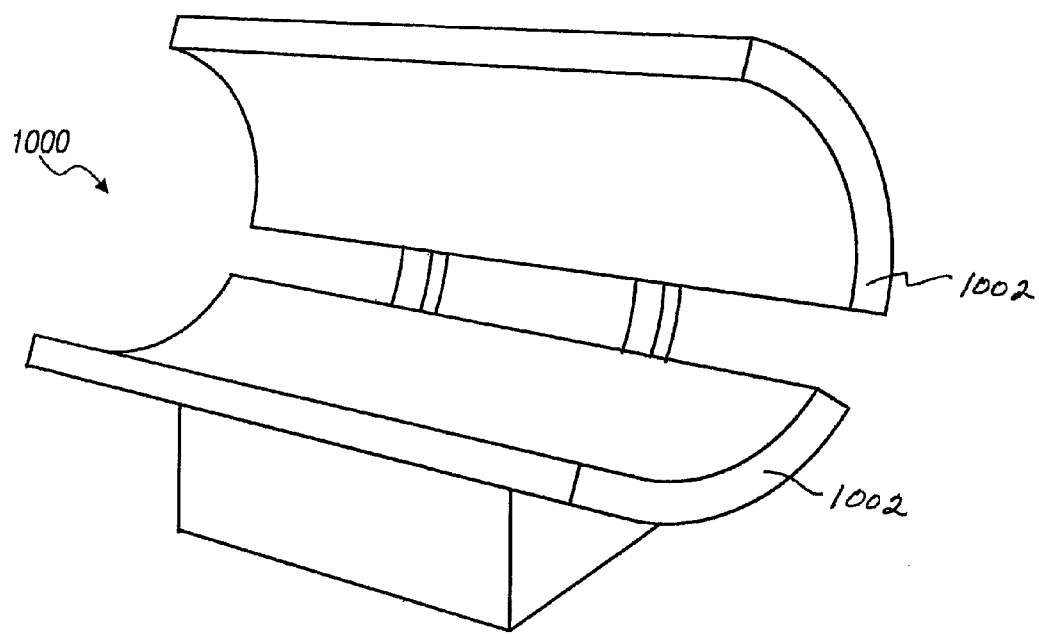
FIGS. 10 and 11 represent a mattress disinfecting apparatus.
Figure 11:
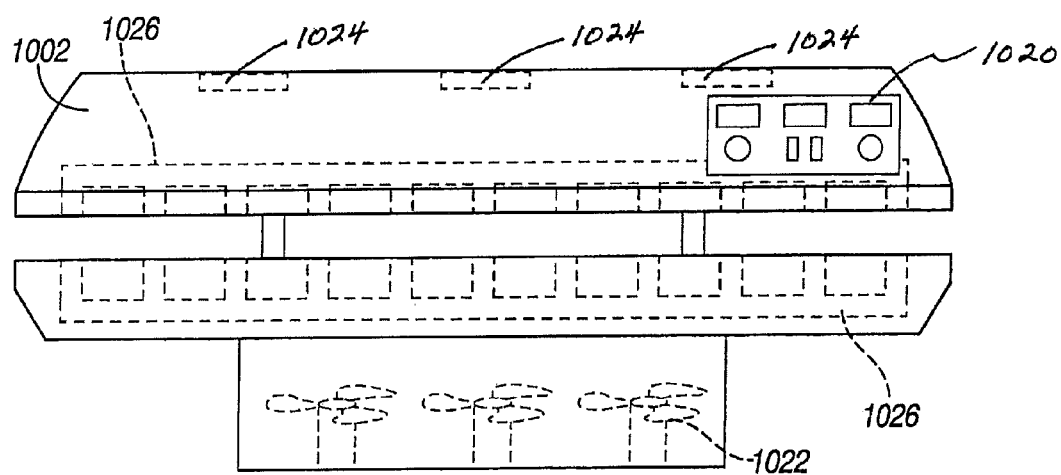

FIGS. 10 and 11 represent a mattress sterilizer 1000 according to the present teachings. The sterilizer 1000 has a pair of closable members 1002 hingeably coupled which function to apply UV-C radiation to the mattress. Additionally, the mattress sterilizer 1000 functions to apply heat and pressure to the mattress to bring the mattress to a temperature to kill pathogens. It is envisioned the sterilizer 1000 can have a bag associated therewith to contain the heat therein.

The system 1000 has controls 1020 which control a plurality of fans 1022 and vent exhausts 1024. Further associated with the controller 1020 is a plurality of UV-C emitters 1026 which function as described in any of the examples above. While shown in a horizontal configuration, it is envisioned the members can be horizontally positioned.

Figure 12:
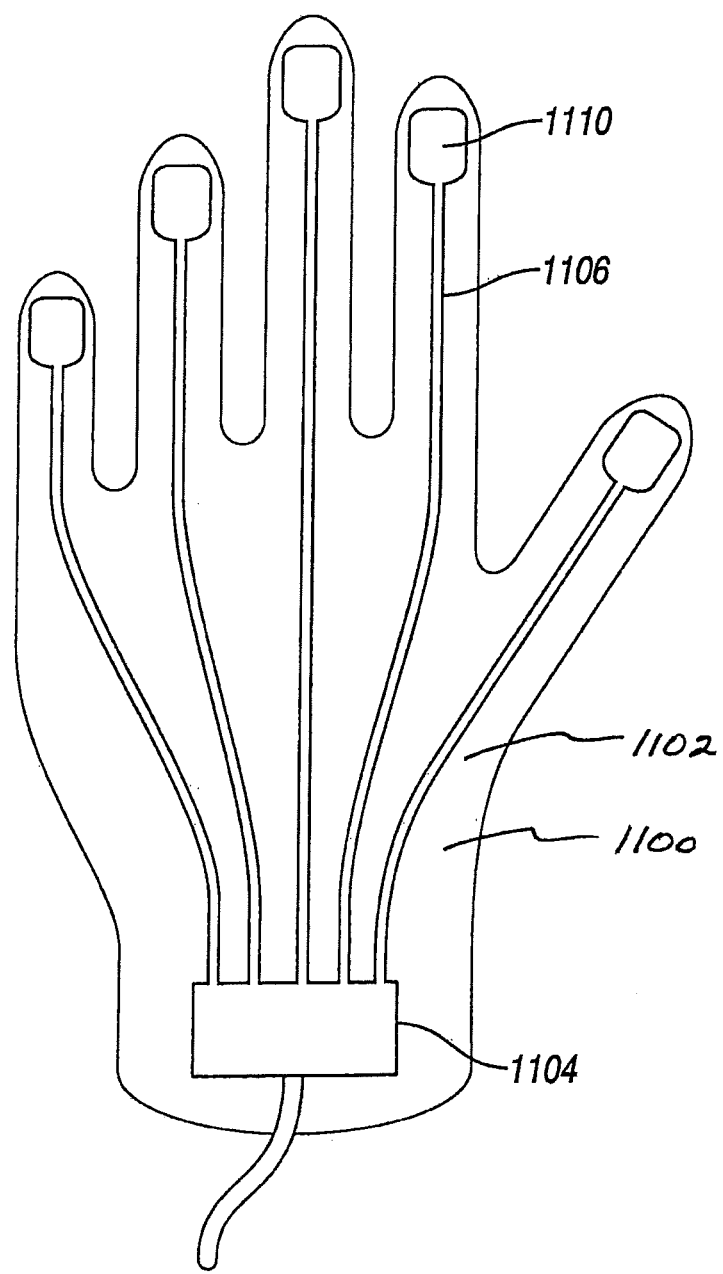
Figure 13A:
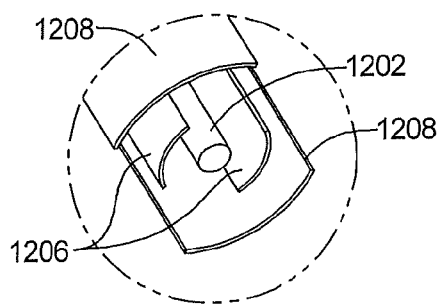
FIGS. 13a-13i represent UV lamp ozone cartridges used in the systems according to the present teachings.
Figure 13B:
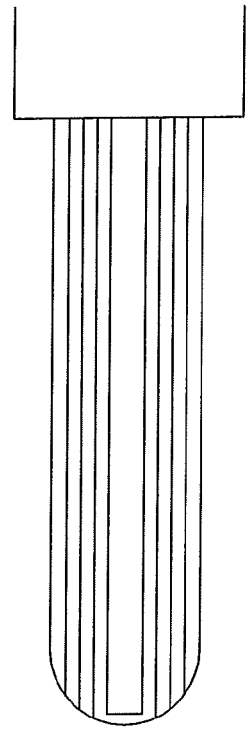
Figure 13C:
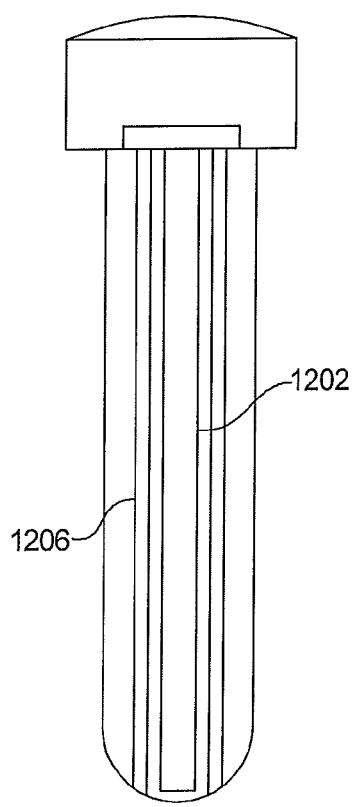
Figure 13D:
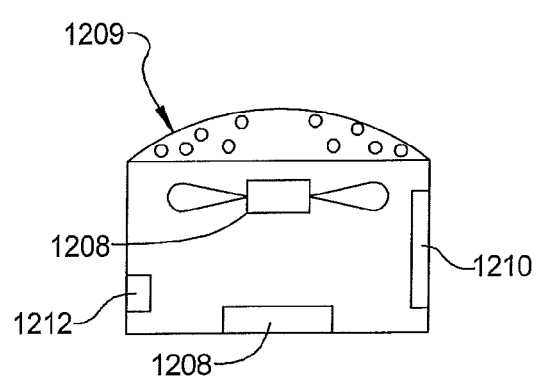
Figure 13E:
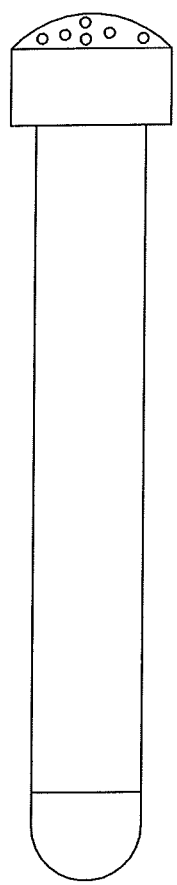
Figure 13F:
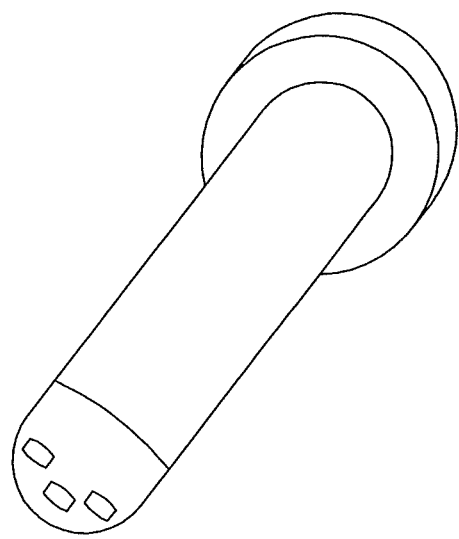
Figure 13G:
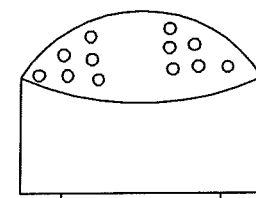
Figure 13H:
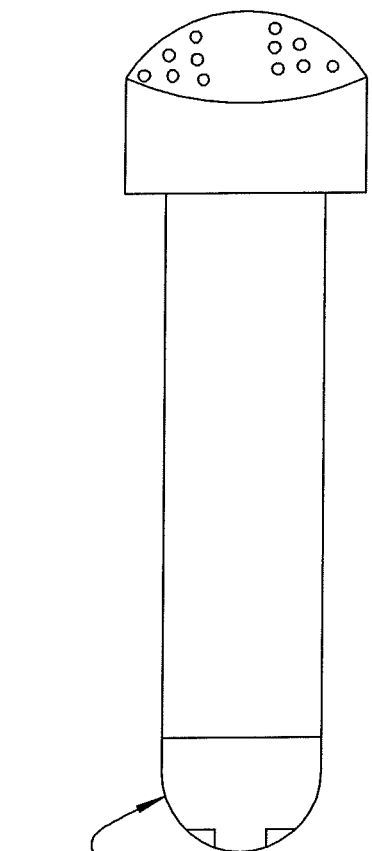
Figure 13I:
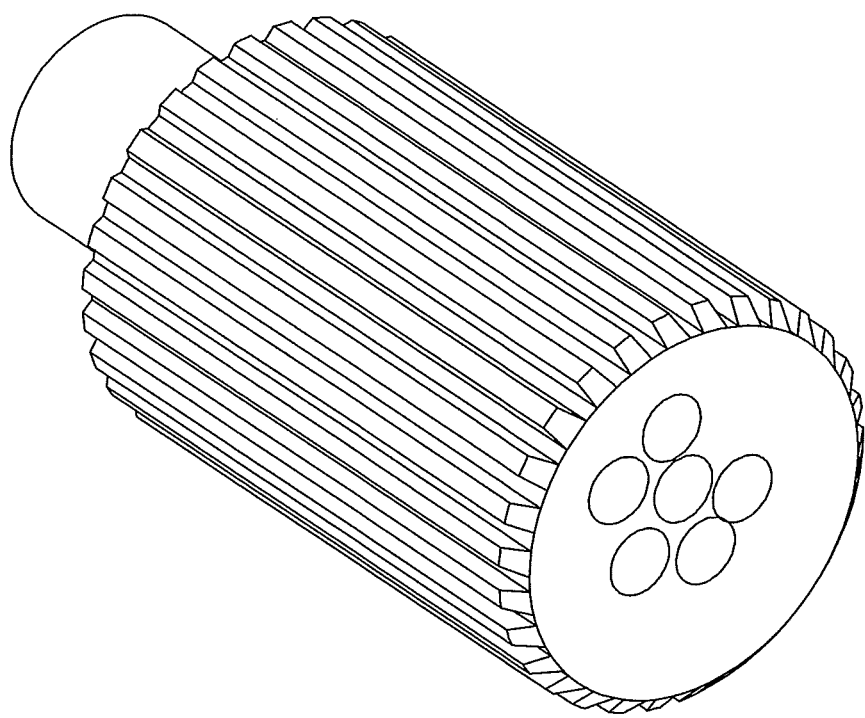

FIG. 12 represents an alternate garment dryer 1100 according to the present teachings. The dryer 1100 has a hand shaped body 1102. The body 1102 has an associated UV-C emitter 1104, fiber optic cables 1106, and UV emitters 1110 which function to apply UV-C light to various portions of the exterior surface of the hand shaped body 1102. The LED source can be, for instance, a LED matrix source as described in U.S. Pat. No. 7,328,708 incorporated herein by reference.

FIGS. 13a-13i represent modular components 1200 which are used to supply UV radiation and/or ozone. The components 1200 have a gas filled tube 1202 or LED which supplies UV radiation. Optionally, the UV radiation is directed to a coated (horizontal or vertical) surface 1206 which functions to produce ozone. Optionally, the components 1200 can have a fan 1208 and adjustable baffle 1209 which will disperse the ozone about the garment or textile product being dried or sanitized. Adjustable baffles can be used to regulate the air flow. Associated with each component 1200 can be a solar cell 1208 and rechargeable battery 1210. Optionally, any of the components can be powered by A/C or D/C power source 1212 such as from a vehicle cigarette lighter, or a solar panel. Safing switches can be incorporated which will disable the UV source should any of the systems be disassembled.

Figure 14A:
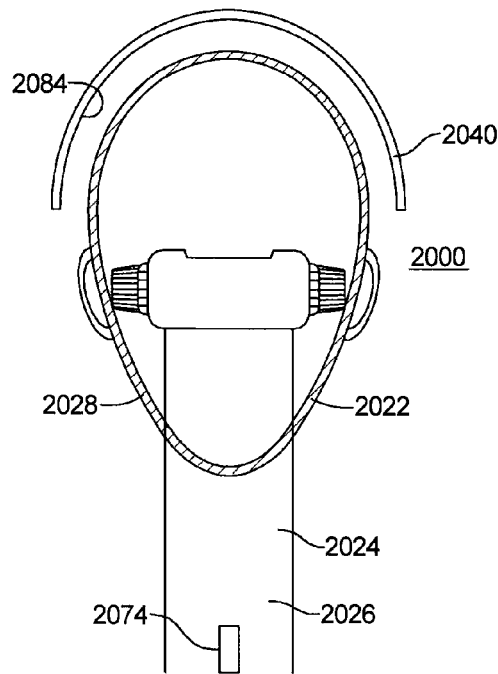
FIGS. 14a-14d represent a head gear dryer according to the present teachings.
Figure 14B:
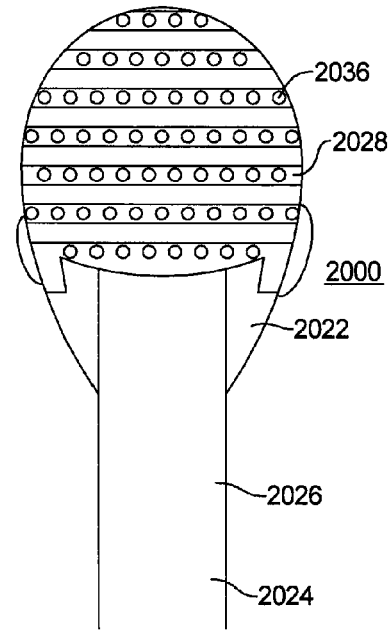
Figure 14C:
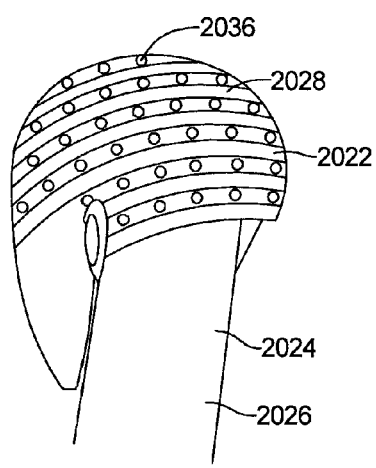
Figure 14D:
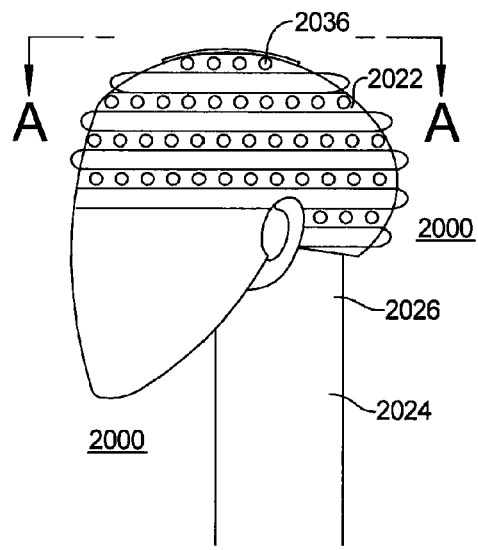

FIGS. 14a-16c represent a head gear dryer 2000 according to the present teachings. The head gear dryer 2000 is illustrated in FIGS. 14a-14c having at least one main member 2022, at least one conduit 2024, and a base 2026. Each of the main members 2022 are in communication with one of the conduits 2024. The conduit portion 2024 may additionally be perforated to allow air flow into the wrist portion of the glove. Optionally, these perforations may be baffled to regulate air flow. In the illustration as shown, the main members 2022 each include an outer surface 2028 that is configured for receiving the head gear. It should be noted that the main members 22 can be solid, or can be deformable to accept a varying array of head gears, such as an athletic or motor cycle helmet.

The main members 22 each include at least at a first member 2030 for receiving a crown of a head gear, a second member 2032 for receiving a neck portion of the head gear, and a third member 2034 for receiving the remaining head covering. The main members 2022 also include a plurality of apertures 2036 that are disposed along the outer surface 2028. The main members 2022 also include an adjustable baffle 60. As discussed in greater detail below, the baffle 60 is to increase or decrease air flow inside of the main member 22.

As best seen in FIG. 14A, the main member 2022 is contoured along a curved axis A-A. The curved axis A-A is contoured to match the hooked configuration of a helmet 2040. That is, the main members 2022 are in a hooked configuration, and adapted to fit under the head gear 2040. Having the main members 2022 contoured along the curved axis A-A is advantageous, because when the head gear 2040 is placed on one of the main members 2022, the head gear 2040 is dried and disinfected while in the hooked configuration, as discussed in greater detail below. That is, the main member 2022 is configured such that the head gear 2040 can be dried in the natural shape.

Figure 15:
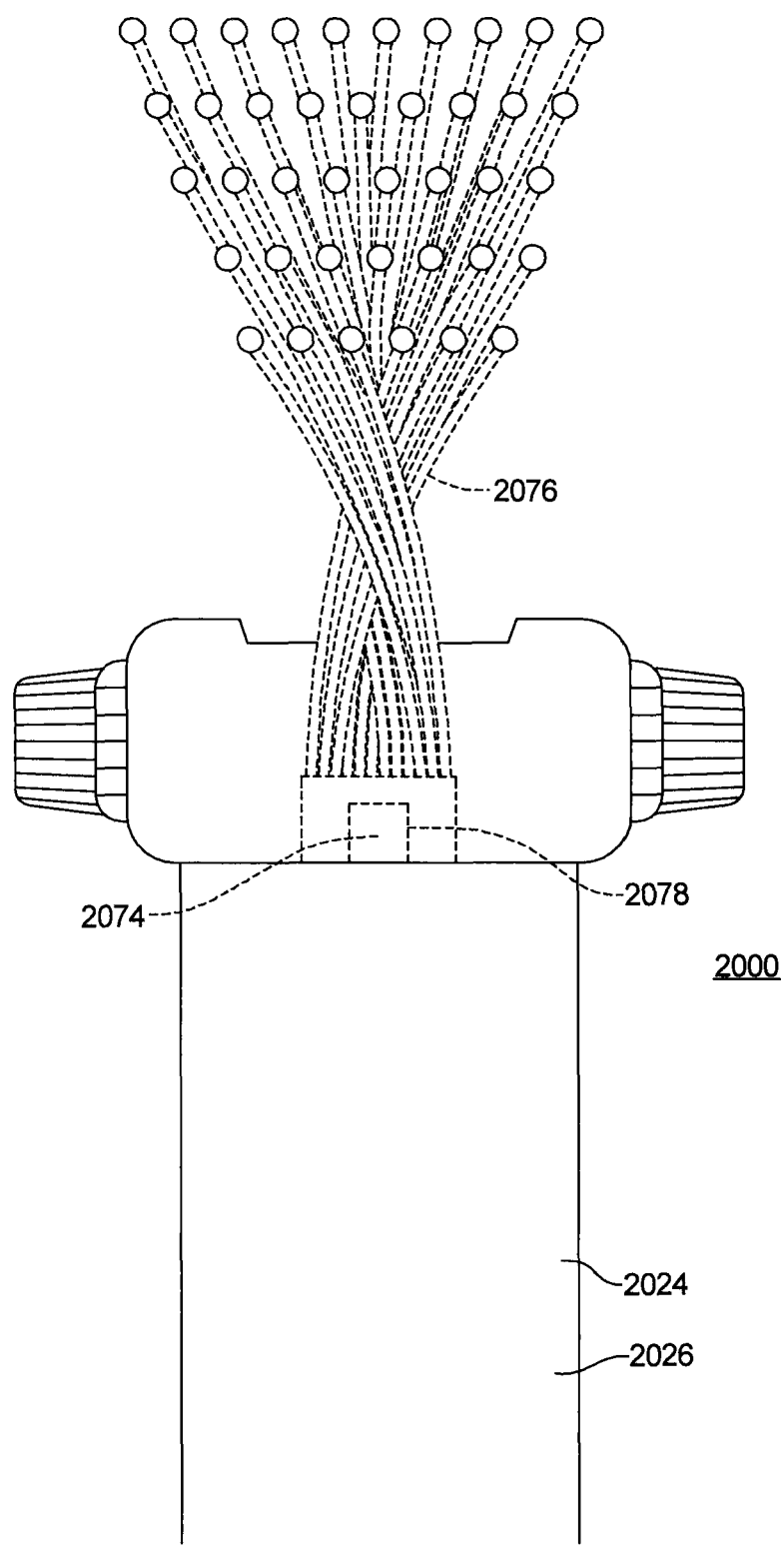
FIGS. 15-16c represent components of the head gear dryer.
Figure 16A:
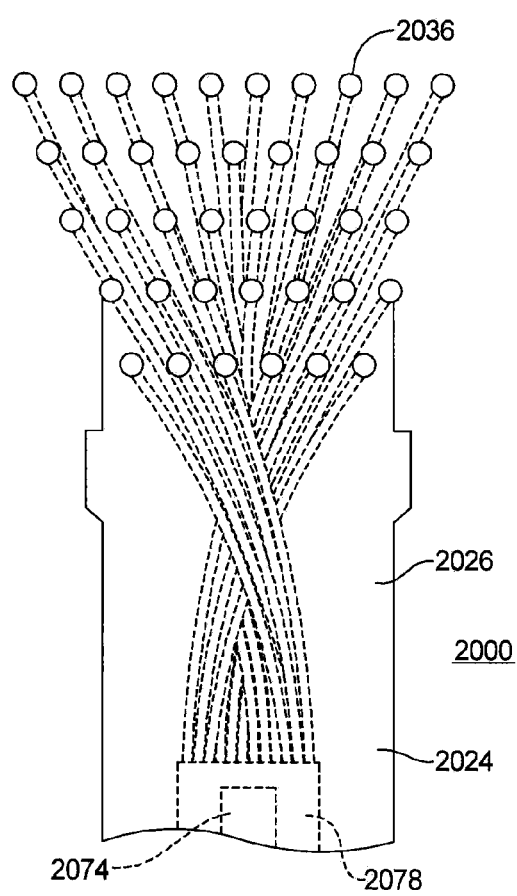
Figure 16B:
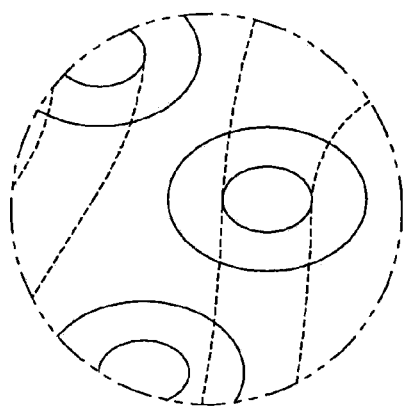
Figure 16C:
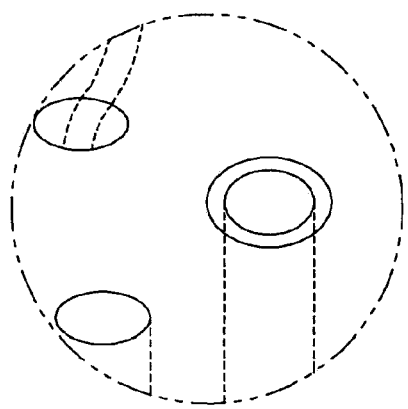

FIGS. 15-16c are partially sectional views of the conduits 2024 and the base 2026. The main members 2022 may be removable from the conduits 2024. For example, in some cases it may be easier to clean the main member 2022 by removing the main members 2022 from the conduits 2024 first. A passageway 2076 is located inside of the base 2026 and connects one of the conduits 2024 to the other conduit 2024. An air source, such as a fan 70, is used to generate airflow to both the conduits 2024 which, in turn, are in communication with the main members 2022. The fan 70 as an air source, it should be noted that any device capable of producing airflow may be used. As shown with respect to FIGS. 1 and 2, the baffle 60, is used to regulate the amount of airflow to the inside surface 2084 of the head gear 2040 and, therefore, the amount of air from the fan 70 can be increased or decreased, depending on what the user desires.

As previously described above, the ultraviolet light source 74 is included in the head gear dryer 2000 as well. The ultraviolet light source 74 emits UV-C light (also known as germicidal UV light). UV-C is ultraviolet light in the C bandwidth of the ultraviolet light spectrum. Ultraviolet irradiation in the C bandwidth (UV-C) is used for disinfection purposes because the UV-C light kills microorganisms, mold and bacteria that are trapped inside of the head gear 40. In one example, the ultraviolet light source 74 is a mercury-vapor lamp that emits UV-C light; however, it should be noted that any light source that emits UV-C rays may be used as well. In one illustration, the ultraviolet light source 74 also produces ozone ($O_3$); however, an ultraviolet light source 74 that does not produce ozone may be used as well. Ozone and UV-C light are combined with moisture that is trapped inside the head gear 2040 to remove odors. More specifically, the combination of ozone and UV-C light with moisture produces chemicals, such as hydroxyl radicals (—OH), which are purifying agents that neutralize unpleasant odors that are trapped inside of the head gear 40.

It should be noted that prolonged exposure to UV-C light that is emitted from the ultraviolet light source 74 may be harmful to humans. As a result, as seen in FIGS. 14a-14d, a safety device 2078 is included along the outer surface 2028 of the main members 2022. The safety device 2078 detects if the head gear 2040 is installed on the main member 22. The ultraviolet light source 2074 is unable to emit UV-C light unless the head gear 2040 is secured to the main member 2022. In the illustration as shown in both of FIGS. 1-2, the safety device 2078 is located on the third member 2034. However, it should be noted that the safety device 2078 may be located anywhere along the main member 2022. In one illustration, the safety device 2078 is a sensor that detects the presence of the head gear 2040 along the outer surface 2028. However, the safety device 2078 can be any device that is able to detect whether the head gear 2040 is installed along the outer surface 2028 of the main member 2022. More than one safety sensor 2078 can also be applied along the outer surface 2028 of each of the main members 2022 as well. In another example, the safety device 2078 can be a shield or a hood that protects against UV-C light that is well-known in the art, and covers the main members 2022 when in use.

As described above, because the head gear 2040 may contain salt that is emitted from a user's hand, the head gear dryer 20 may also include a spray source 80. The spray source 80 is filled with a solution 82 that breaks down salt that collects inside of the head gear 40. The solution 82 may also include ingredients that are used to deodorize the inside of the head gear 40 such as, but not limited to, cyclodextrin. Additionally, the solution 82 may also include an ingredient to the inside of the head gear 40 such as, but not limited to, isopropyl alcohol or chloroxylenol. In one illustration, the solution 82 may include each of the ingredients that breakdown salt, deodorize the inside of the head gear 40, and also disinfect the inside of the head gear 40. Alternatively, the solution 82 may only include one of the ingredients that break down salt, disinfect, and deodorize. The solution 82 is applied to the inside of the head gear 40 after UV-C light from the ultraviolet light source 74 reduces microorganisms, mold, and bacteria that are trapped inside of the head gear 40, as discussed in greater detail below.

Figure 17:
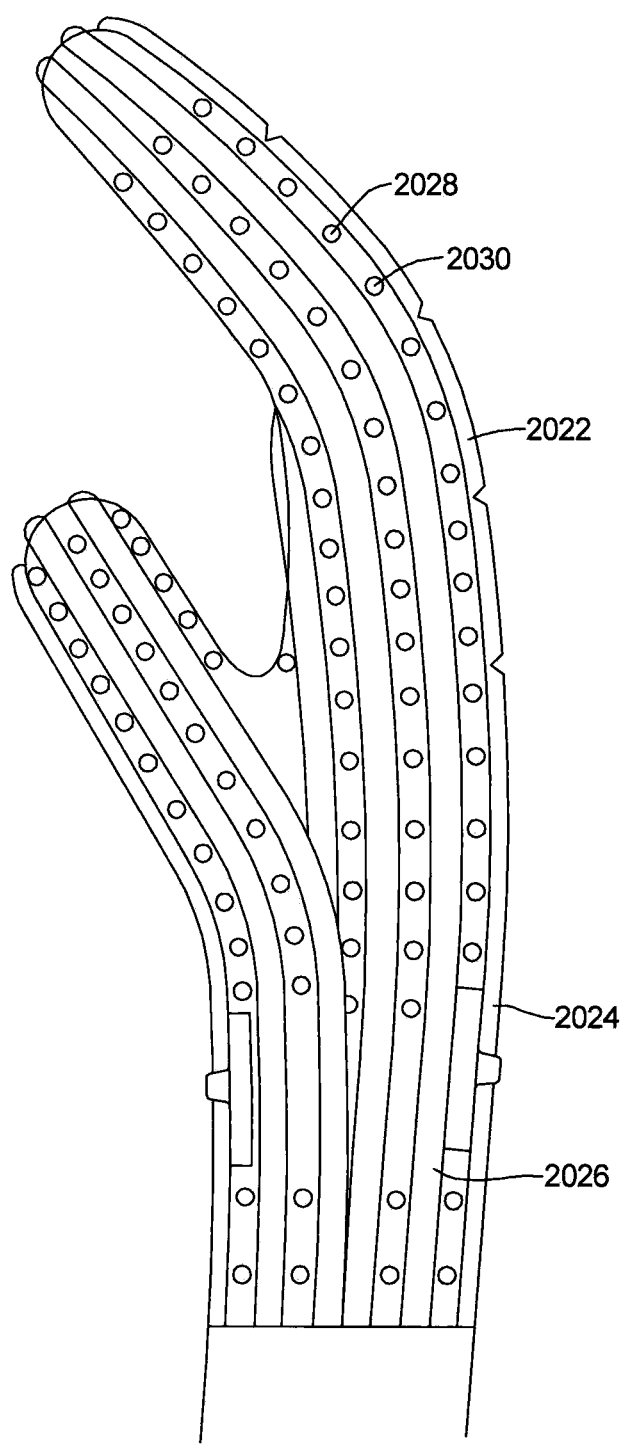
FIG. 17 represents a glove dryer according to the present teachings.

FIG. 17 represents a glove dryer according to the present teachings. It can incorporate all of the features described above with respect to glove dryers. Additionally, the base member can be formed of flexible. Breaking points make the joints more flexible to accommodate a fingered glove.

Figure 18A:
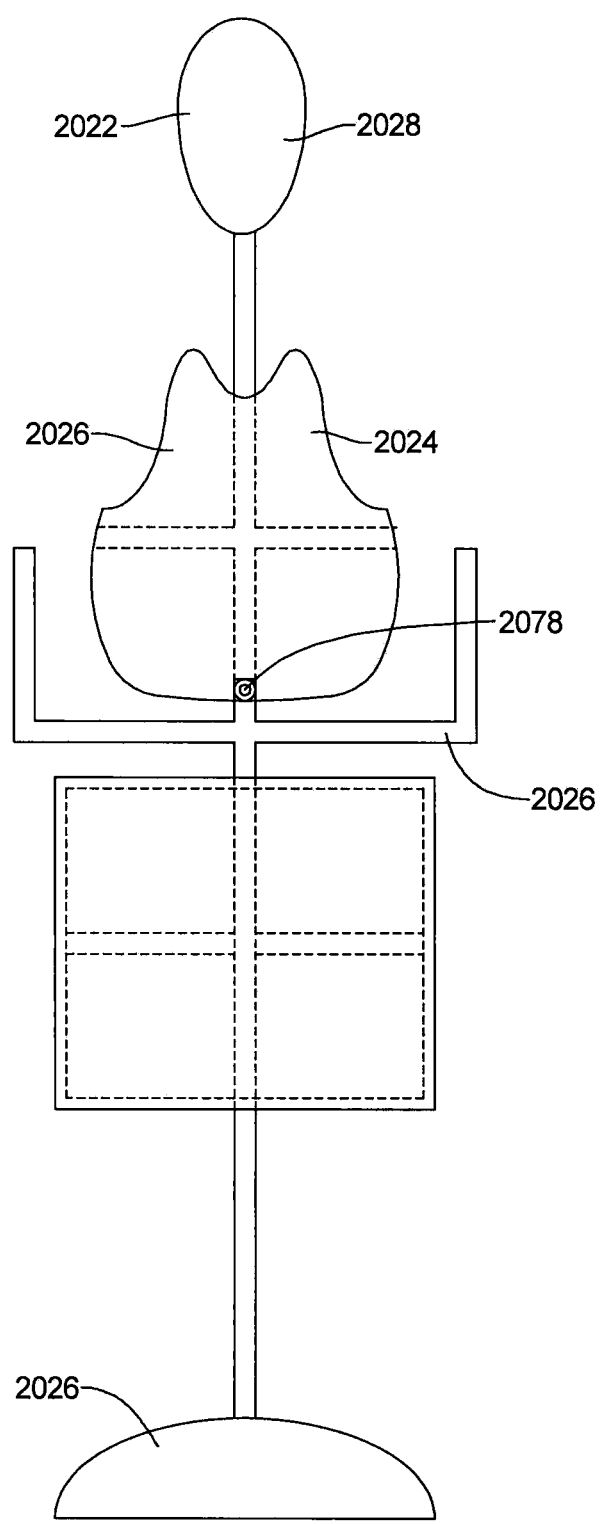
FIGS. 18a-18c represent an athletic suit dryer according to the present teachings.
Figure 18B:
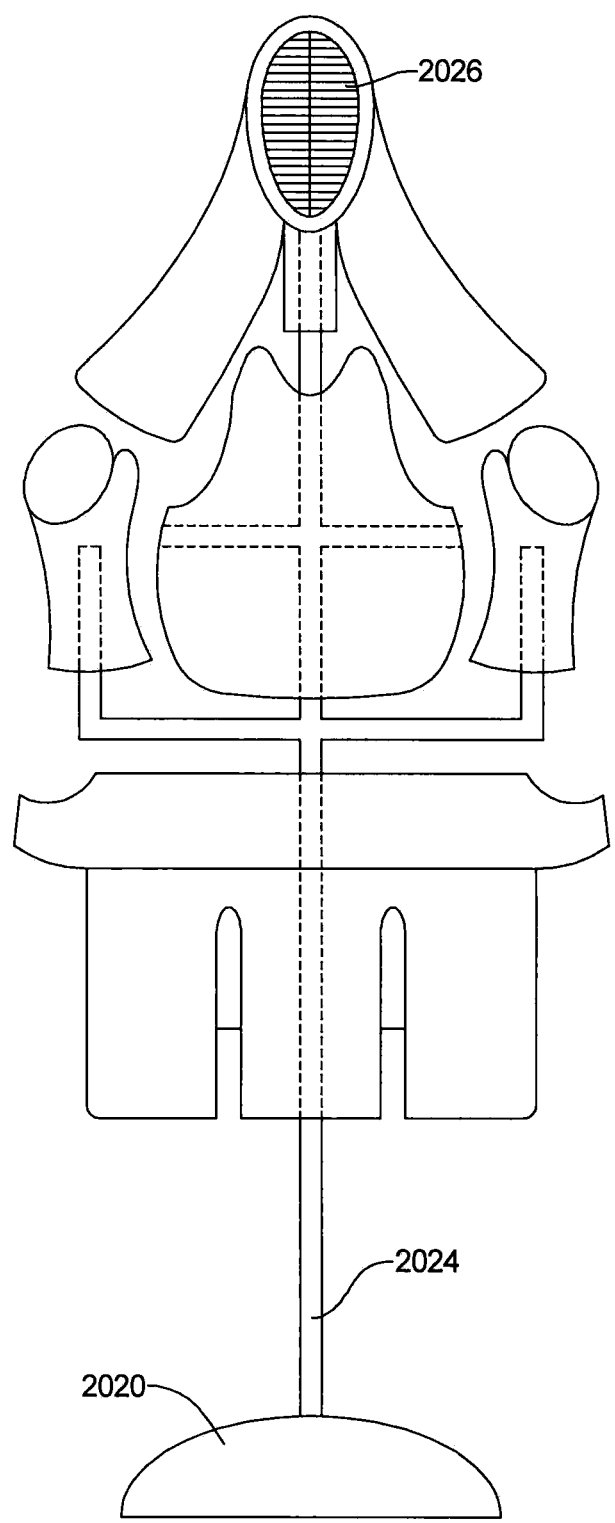
Figure 18C:
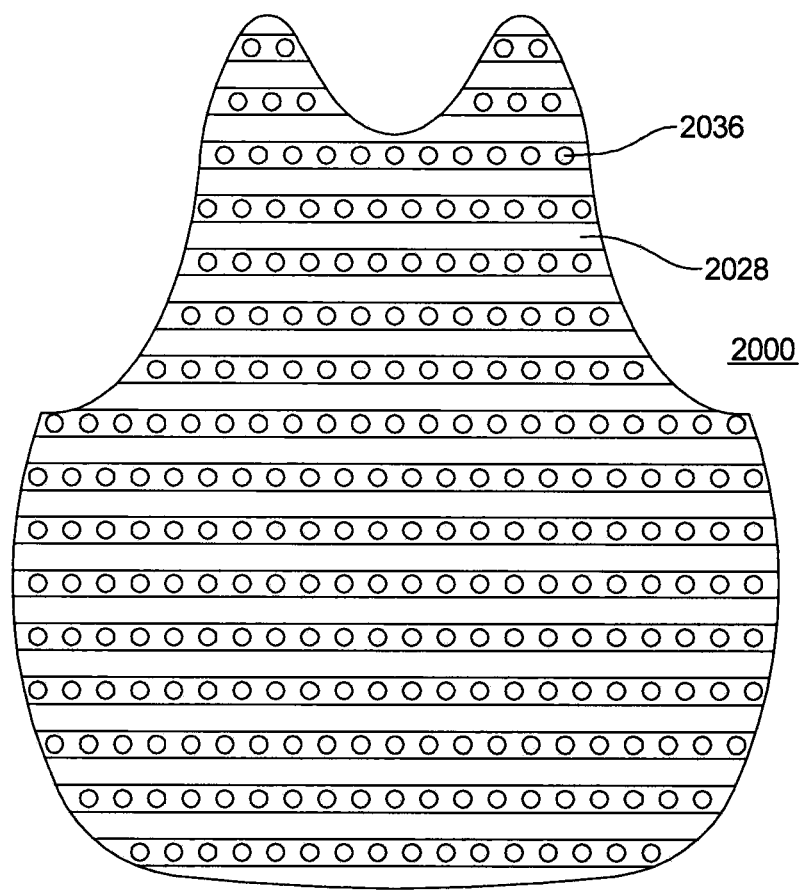

FIGS. 18a-18c represent an athletic suit dryer according to the present teachings. Specifically, the FIGS. 14a-14d illustrates the main members 22 configured to receive a head gear and armor and, more specifically, the outer surface 28 is configured to receive a head gear and armor that is used in the Japanese sport of kendo (Kendo Bogu). Shown is the head form as described above. Also shown in FIG. 15b is a drying system as described above configured to dry, the men combined face mask and shoulder protectors (helmet); kote; hand and forearm protectors (gauntlets); dō: torso protector (breastplate); tare: groin and leg protectors (faulds); and A fifth component, sune-ate (shin protectors, or greaves), are worn by naginatajutsu practitioners. FIG. 18c represents a portion of the dryer configured to dry the torso protector.

Figure 19:
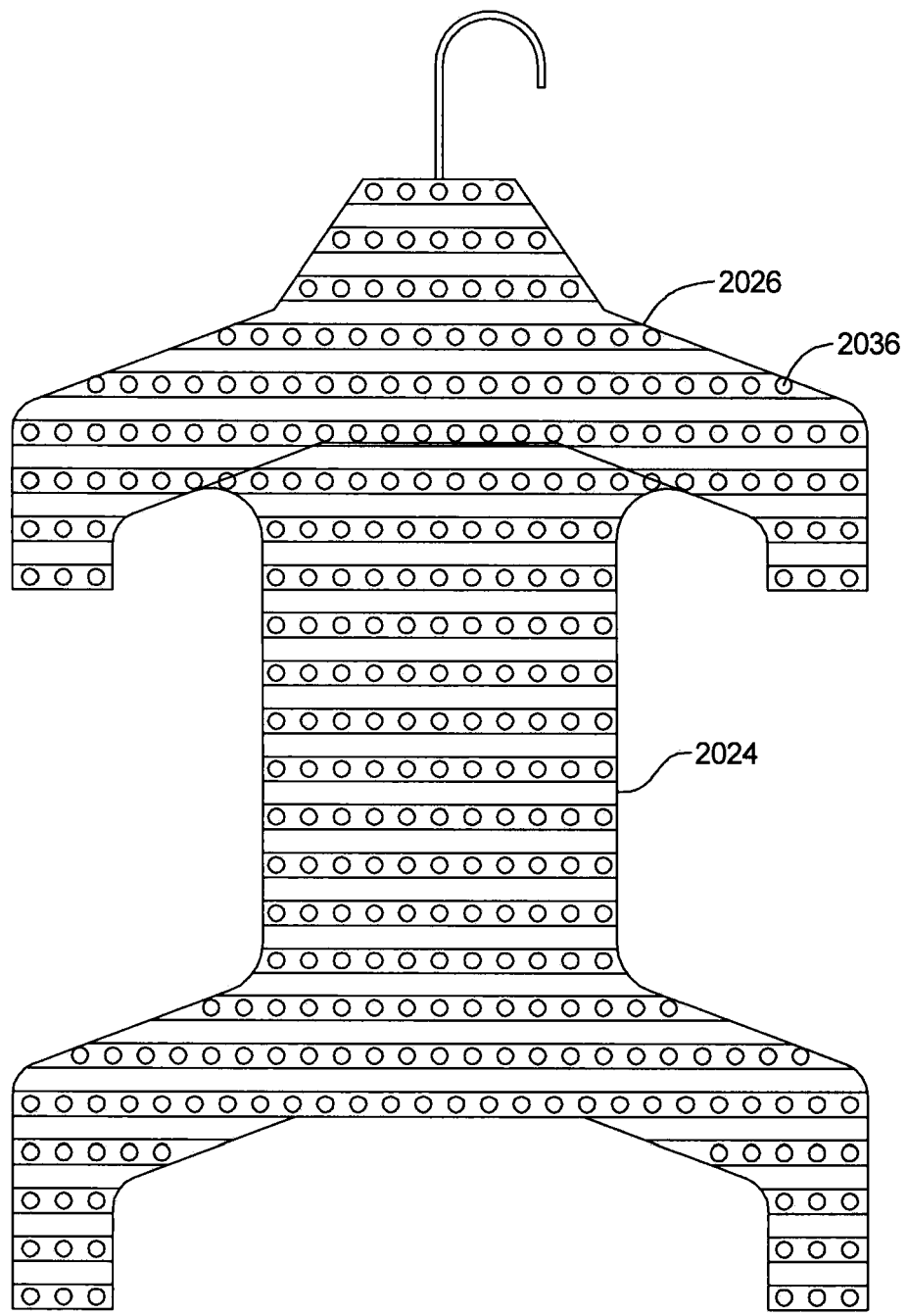
FIG. 19 represents an athletic suit dryer according to the present teachings.

FIG. 19 represents an athletic suit dryer according to the present teachings. The athletic suit dryer has a plurality of air hold coupled to a pressurized air sour or fan (not shown). Also included can be a source of ozone as described above.

Figure 20A:
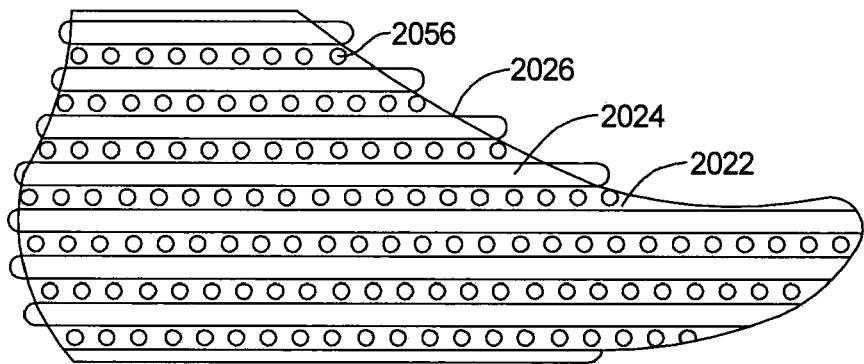
FIGS. 20A-20B represent footwear dryer according to the present teachings.
Figure 20B:
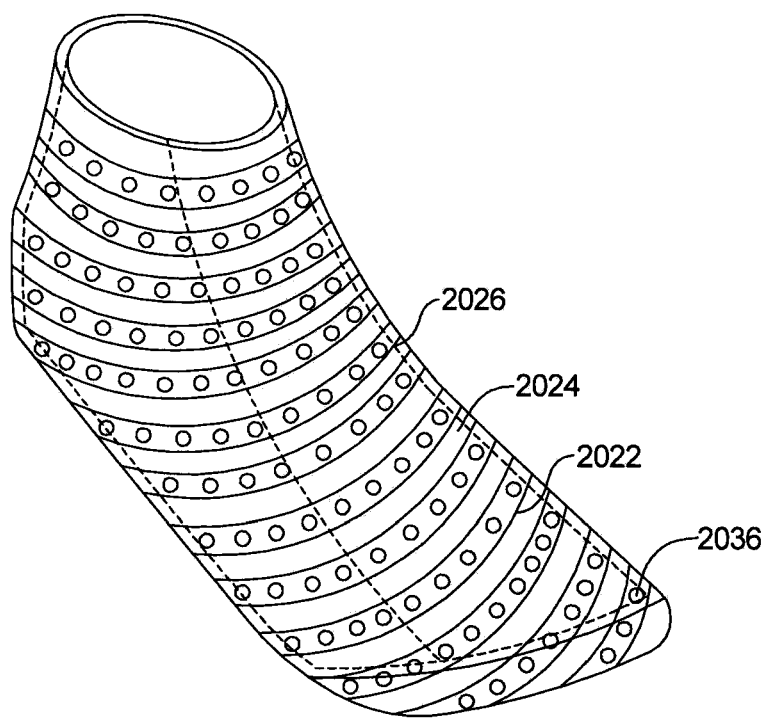
Figure 21A:
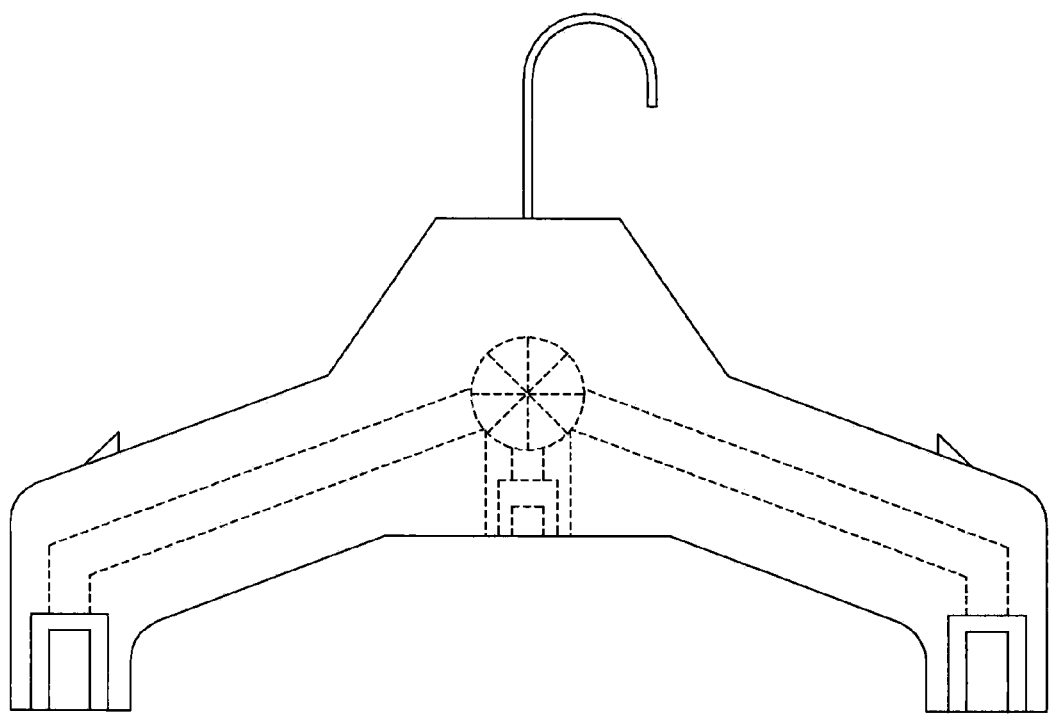
FIGS. 21A-24 represent alternative dryers according to the present teachings.
Figure 21B:
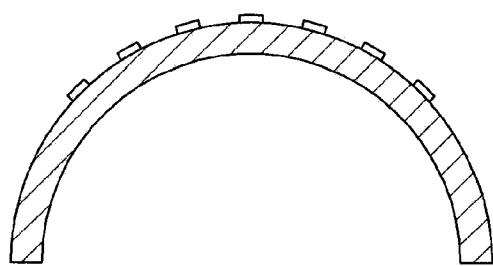
Figure 21F:
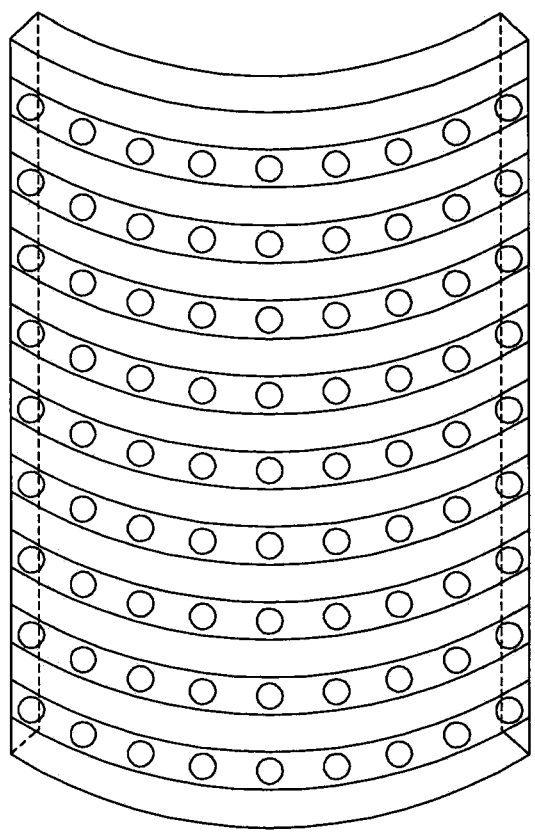
Figure 22:
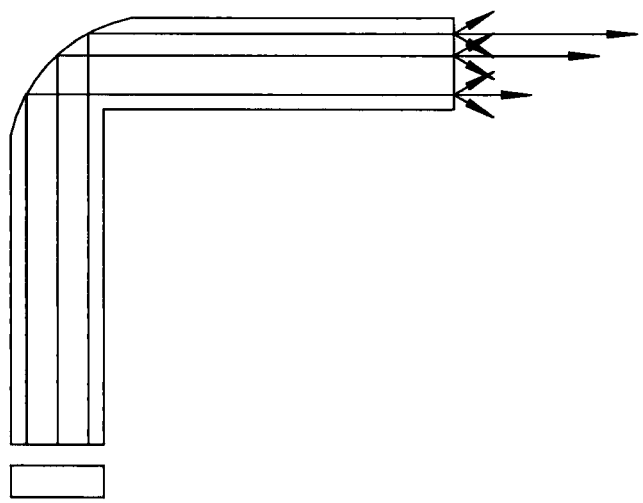
Figure 23A:
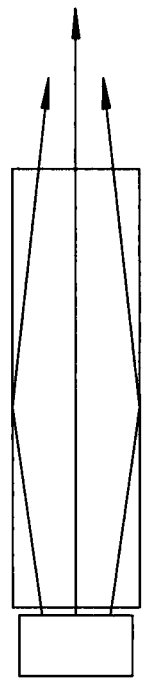
Figure 23B:
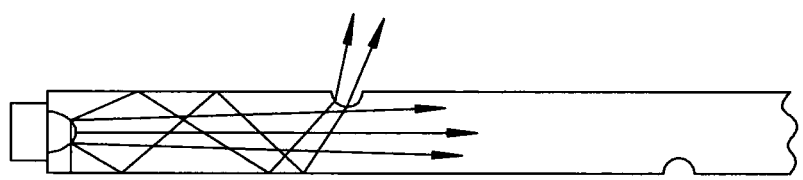
Figure 24:
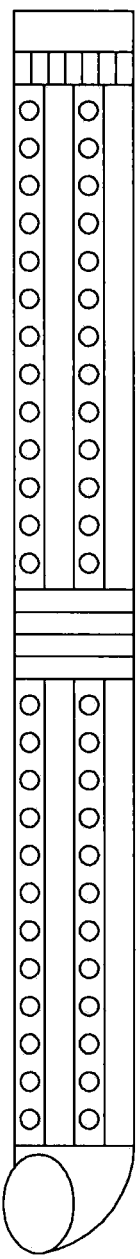
Figure 25A:
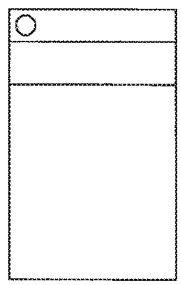
Figure 25B:
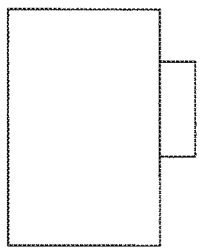
Figure 25C:
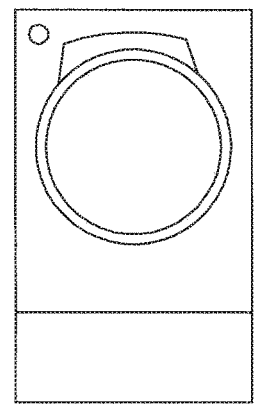
Figure 25:
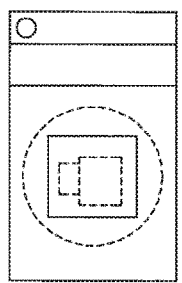
Figure 25D:
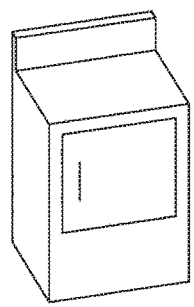

FIGS. 20a-20B represent footwear dryer according to the present teachings. As previously described above, the ultraviolet light source (not shown) is included in the footwear dryer 2000' as well. The footwear dryer can have a deformable body member. The ultraviolet light source emits UV-C light (also known as germicidal UV light). UV-C is ultraviolet light in the C bandwidth of the ultraviolet light spectrum. Ultraviolet irradiation in the C bandwidth (UV-C) is used for disinfection purposes because the UV-C light kills microorganisms, mold and bacteria that are trapped inside of the foot wear. In one example, the ultraviolet light source is a mercury-vapor lamp that emits UV-C light; however, it should be noted that any light source that emits UV-C rays may be used as well. In one illustration, the ultraviolet light source 74 also produces ozone ($O_3$); however, an ultraviolet light source 74 that does not produce ozone may be used as well. Ozone and UV-C light are combined with moisture that is trapped inside the footwear to remove odors. More specifically, the combination of ozone and UV-C light with moisture produces chemicals, such as hydroxyl radicals (—OH), which are purifying agents that neutralize unpleasant odors that are trapped inside of the footwear.

FIGS. 20A-24 represent alternative dryer according to the present teachings. The dryer includes a modular design which allows the coupling to various members to a hanger shaped base. As seen in FIGS. 21*c*-21*f*, the attachable members can be conduits for drying air and ozone and can have baffles to restrict the flow of air. As described above and shown in FIGS. 22-24, UV light can be coupled to the members using light piping. The surface of the additional members can be textured to effect the spread of UV light. Additionally, the UV sources described above can be coupled to the hanger shaped base. It should be noted that prolonged exposure to UV-C light that is emitted from the ultraviolet light source 74 may be harmful to humans.

FIGS. 25*a*-25*e* and 26 represent a cloths dyer according to the present teachings. The dryer includes an incorporated UV source used too disinfect clothing in the dryer drum. The dryer will include an emitter and a darkened dryer door. Optionally, the emitter can be included into a rim of the dryer door.

Each of the afore-described embodiments can utilize forced heated air or convection air flow. Drying time can be set by a timer to shut off the fan or heating coil if desired. Fan direction can be reversed to create a vacuum effect to draw moisture out of the textile product. It is envisioned a tree-type structure having any of the aforementioned structures disposed thereon.

The body structures can be pliable or can have a catalytic oxidation surface such as silver, nickel or copper. Optionally, low output ozone emitters can be used to suppress bacterial growth, mold growth, viruses, odors, and skin cells. When functioning, low level ozone is converted to peroxides ($H_2O_2$), hydroxyl ions ($OH^-$), super oxide ions ($O_2^-$) and ozonide ions ($O_3^-$) by the catalytic surface and high intensity UV-C light. Optionally, nanotechnology can be used to produce the ozone. In this regard, the nanoparticles can be illuminated with UV light which converts oxygen into ozone. Additionally, hydroxyl, hydrogen peroxide, superoxide, and ozonide ions can be utilized.

While shown for drying and sterilizing gloves, it is envisioned the teachings can be applied to drying boots and thickly padded gloves such as hockey or ski gloves. Optionally, a spray atomizer with disinfecting solution can be associated with the fan.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

While the present disclosure has been particularly shown and described with reference to the foregoing preferred illustrations, it should be understood by those skilled in the art that various alternatives to the illustrations of the disclosure described herein may be employed in practicing the disclosure without departing from the spirit and scope of the disclose as defined in the following claims. For example, the system described can include a remote control. Optionally, the system can utilize multiple drying or disinfecting structures in the form of a tree. It is intended that the following claims define the scope of the disclosure illustrations within the scope of these claims and their equivalents be covered thereby. This description of the disclosure should be understood to include all novel and non-obvious combinations of elements described herein, and claims may be presented in this or a later application to any novel and non-obvious combination of these elements. The foregoing embodiment is illustrative, and no single feature or element is essential to all possible combinations that may be claimed in this or a later application.

What is claimed is:

1. An apparatus for drying helmets, comprising:
   a main member including an outer surface configured for receiving a helmet, the main member including a plurality of apertures disposed along the outer surface, wherein the main member includes a first member for receiving a crown portion of the helmet;
   at least one optical fiber including an end that emits a UV-C light; and
   at least one air source for blowing air;
   wherein the apertures are in communication with the air source and the optical fiber, and allow air from the air source and UV-C light from the optical fiber to pass through the outer surface, wherein at least one aperture receives the end of the optical fiber.

2. The apparatus as recited in claim 1, further comprising a spray source for spraying a solution, the spray source in communication with the apertures.

3. The apparatus as recited in claim 1, wherein the light source produces an ozone, and the ozone is in communication with the apertures.

4. A method of drying a helmet, comprising the steps of:
   placing a helmet on a main member, the main member including a plurality of apertures disposed along an outer surface, at least one light source for emitting a UV-C light, and at least one air source for blowing air;
   drying the helmet by air from the air source through the apertures, wherein the apertures are in communication with the air source and allow air to pass through the outer surface; and
   emitting UV-C light from the light source, wherein the main member is configured to at least partially allow UV-C light to pass through the outer surface.

5. The method as recited in claim 4, further comprising the step of allowing communication between the apertures and the light source to allow for UV-C light to pass through the outer surface.

6. The method as recited in claim 4, further comprising the step of producing an ozone, wherein the light source produces the ozone, and the ozone is in communication with the apertures.

7. The method as recited in claim 4, further comprising the step of spraying a solution from a spray source, the spray source in communication with the apertures, and wherein the solution is sprayed after UV-C light from the ultraviolet light source is emitted.

* * * * *